(12) United States Patent
Green et al.

(10) Patent No.: US 6,791,264 B2
(45) Date of Patent: Sep. 14, 2004

(54) LIGHT-EMITTING PANEL AND A METHOD FOR MAKING

(75) Inventors: Albert Myron Green, Springfield, VA (US); Adam Thomas Drobot, Vienna, VA (US); Edward Victor George, Lake Arrowhead, CA (US); Roger Laverne Johnson, Encinitas, CA (US); Newell Convers Wyeth, Oakton, VA (US)

(73) Assignee: Science Applications International Corporation, San Diego, CA (US)

( * ) Notice: Subject to any disclaimer, the term of this patent is extended or adjusted under 35 U.S.C. 154(b) by 0 days.

(21) Appl. No.: 10/303,926

(22) Filed: Nov. 26, 2002

(65) Prior Publication Data

US 2003/0094891 A1 May 22, 2003

Related U.S. Application Data

(62) Division of application No. 09/697,344, filed on Oct. 27, 2000, now Pat. No. 6,612,889.

(51) Int. Cl.[7] .................................................. H01J 17/49
(52) U.S. Cl. ........................ 313/582; 313/584; 313/495; 313/586
(58) Field of Search ................................. 313/582, 585, 313/586, 587, 495

(56) References Cited

U.S. PATENT DOCUMENTS

| | | | | |
|---|---|---|---|---|
| 3,704,386 A | * | 11/1972 | Cola | ........................... 313/585 |
| 4,563,617 A | * | 1/1986 | Davidson | ..................... 315/312 |
| 5,808,403 A | | 9/1998 | Clerc | .......................... 313/336 |
| 5,939,826 A | * | 8/1999 | Ohsawa et al. | ............. 313/582 |
| 6,577,056 B1 | * | 6/2003 | Chang | ......................... 313/582 |

FOREIGN PATENT DOCUMENTS

| WO | WO 00/36465 | 6/2000 | ........... G02F/1/167 |
|---|---|---|---|

OTHER PUBLICATIONS

Preliminary Examination Report for Application No. PCT/US01/42803, dated Sep. 22, 2003 (mailing date).
Preliminary Examination Report for Application No. PCT/US01/42782, dated Jun. 4, 2003.
International Search Report for Application No. PCT/US01/42805, dated Apr. 3, 2003 (mailing date).
International Search Report for Application No. PCT/US01/42803, dated Dec. 9, 2002 (mailing date).
Written Opinion for Application No. PCT/US01/42805, dated Apr. 2, 2004 (mailing date).

* cited by examiner

*Primary Examiner*—Nimeshkumar D. Patel
*Assistant Examiner*—Mariceli Santiago
(74) *Attorney, Agent, or Firm*—Kilpatrick Stockton LLP

(57) ABSTRACT

An improved light-emitting panel having a plurality of micro-components sandwiched between two substrates is disclosed. Each micro-component contains a gas or gas-mixture capable of ionization when a sufficiently large voltage is supplied across the micro-component via at least two electrodes. An improved method of manufacturing a light-emitting panel is also disclosed, which uses a web fabrication process to manufacturing light-emitting displays as part of a high-speed, continuous inline process.

29 Claims, 22 Drawing Sheets

LIGHT-EMITTING PANEL AND A METHOD FOR MAKING

CROSS-REFERENCE TO RELATED APPLICATIONS

This application is a divisional application of and claims priority to and incorporates by reference in its entirety, application Ser. No. 09/697,344 now U.S. Pat. No. 6,612,889, entitled, "A Light-Emitting Panel and a Method for Making," filed Oct. 27, 2000. Also referenced hereby are the following applications which are incorporated herein by reference in their entireties: U.S. patent application Ser. No. 09/697,358 entitled *A Micro-Component for Use in a Light-Emitting Panel* filed Oct. 27, 2000; U.S. patent application Ser. No. 09/697,498 entitled *A Method for Testing a Light-Emitting Panel and the Components Therein* filed Oct. 27, 2000; U.S. patent application Ser. No. 09/697,345 entitled *A Method and System for Energizing a Micro-Component in a Light-Emitting Panel* filed Oct. 27, 2000; and U.S. patent application Ser. No. 09/697,346 entitled *A Socket for Use in a Light-Emitting Panel* filed Oct. 27, 2000.

BACKGROUND OF THE INVENTION

1. Field of the Invention

The present invention is relates to a light-emitting panel and methods of fabricating the same. The present invention further relates to a web fabrication process for manufacturing a light-emitting panel.

2. Description of Related Art

In a typical plasma display, a gas or mixture of gases is enclosed between orthogonally crossed and spaced conductors. The crossed conductors define a matrix of cross over points, arranged as an array of miniature picture elements (pixels), which provide light. At any given pixel, the orthogonally crossed and spaced conductors function as opposed plates of a capacitor, with the enclosed gas serving as a dielectric. When a sufficiently large voltage is applied, the gas at the pixel breaks down creating free electrons that are drawn to the positive conductor and positively charged gas ions that are drawn to the negatively charged conductor. These free electrons and positively charged gas ions collide with other gas atoms causing an avalanche effect creating still more free electrons and positively charged ions, thereby creating plasma. The voltage level at which this ionization occurs is called the write voltage.

Upon application of a write voltage, the gas at the pixel ionizes and emits light only briefly as free charges formed by the ionization migrate to the insulating dielectric walls of the cell where these charges produce an opposing voltage to the applied voltage and thereby extinguish the ionization. Once a pixel has been written, a continuous sequence of light emissions can be produced by an alternating sustain voltage. The amplitude of the sustain waveform can be less than the amplitude of the write voltage, because the wall charges that remain from the preceding write or sustain operation produce a voltage that adds to the voltage of the succeeding sustain waveform applied in the reverse polarity to produce the ionizing voltage. Mathematically, the idea can be set out as $V_s = V_w - V_{wall}$, where $V_s$ is the sustain voltage, $V_w$ is the write voltage, and $V_{wall}$ is the wall voltage. Accordingly, a previously unwritten (or erased) pixel cannot be ionized by the sustain waveform alone. An erase operation can be thought of as a write operation that proceeds only far enough to allow the previously charged cell walls to discharge; it is similar to the write operation except for timing and amplitude.

Typically, there are two different arrangements of conductors that are used to perform the write, erase, and sustain operations. The one common element throughout the arrangements is that the sustain and the address electrodes are spaced apart with the plasma-forming gas in between. Thus, at least one of the address or sustain electrodes is located within the path the radiation travels, when the plasma-forming gas ionizes, as it exits the plasma display. Consequently, transparent or semi-transparent conductive materials must be used, such as indium tin oxide (ITO), so that the electrodes do not interfere with the displayed image from the plasma display. Using ITO, however, has several disadvantages, for example, ITO is expensive and adds significant cost to the manufacturing process and ultimately the final plasma display.

The first arrangement uses two orthogonally crossed conductors, one addressing conductor and one sustaining conductor. In a gas panel of this type, the sustain waveform is applied across all the addressing conductors and sustain conductors so that the gas panel maintains a previously written pattern of light emitting pixels. For a conventional write operation, a suitable write voltage pulse is added to the sustain voltage waveform so that the combination of the write pulse and the sustain pulse produces ionization. In order to write an individual pixel independently, each of the addressing and sustain conductors has an individual selection circuit. Thus, applying a sustain waveform across all the addressing and sustain conductors, but applying a write pulse across only one addressing and one sustain conductor will produce a write operation in only the one pixel at the intersection of the selected addressing and sustain conductors.

The second arrangement uses three conductors. In panels of this type, called coplanar sustaining panels, each pixel is formed at the intersection of three conductors, one addressing conductor and two parallel sustaining conductors. In this arrangement, the addressing conductor orthogonally crosses the two parallel sustaining conductors. With this type of panel, the sustain function is performed between the two parallel sustaining conductors and the addressing is done by the generation of discharges between the addressing conductor and one of the two parallel sustaining conductors.

The sustaining conductors are of two types, addressing-sustaining conductors and solely sustaining conductors. The function of the addressing-sustaining conductors is twofold: to achieve a sustaining discharge in cooperation with the solely sustaining conductors; and to fulfill an addressing role. Consequently, the addressing-sustaining conductors are individually selectable so that an addressing waveform may be applied to any one or more addressing-sustaining conductors. The solely sustaining conductors, on the other hand, are typically connected in such a way that a sustaining waveform can be simultaneously applied to all of the solely sustaining conductors so that they can be carried to the same potential in the same instant.

Numerous types of plasma panel display devices have been constructed with a variety of methods for enclosing a plasma forming gas between sets of electrodes. In one type of plasma display panel, parallel plates of glass with wire electrodes on the surfaces thereof are spaced uniformly apart and sealed together at the outer edges with the plasma forming gas filling the cavity formed between the parallel plates. Although widely used, this type of open display structure has various disadvantages. The sealing of the outer edges of the parallel plates and the introduction of the plasma forming gas are both expensive and time-consuming processes, resulting in a costly end product. In addition, it is particularly difficult to achieve a good seal at the sites where the electrodes are fed through the ends of the parallel plates. This can result in gas leakage and a shortened product lifecycle. Another disadvantage is that individual pixels are not segregated within the parallel plates. As a result, gas ionization activity in a selected pixel during a write operation may spill over to adjacent pixels, thereby raising the undesirable prospect of possibly igniting adjacent pixels. Even if adjacent pixels are not ignited, the ionization activity can change the turn-on and turn-off characteristics of the nearby pixels.

In another type of known plasma display, individual pixels are mechanically isolated either by forming trenches in one of the parallel plates or by adding a perforated insulating layer sandwiched between the parallel plates. These mechanically isolated pixels, however, are not completely enclosed or isolated from one another because there is a need for the free passage of the plasma forming gas between the pixels to assure uniform gas pressure throughout the panel. While this type of display structure decreases spill over, spill over is still possible because the pixels are not in total electrical isolation from one another. In addition, in this type of display panel it is difficult to properly align the electrodes and the gas chambers, which may cause pixels to misfire. As with the open display structure, it is also difficult to get a good seal at the plate edges. Furthermore, it is expensive and time consuming to introduce the plasma producing gas and seal the outer edges of the parallel plates.

In yet another type of known plasma display, individual pixels are also mechanically isolated between parallel plates. In this type of display, the plasma forming gas is contained in transparent spheres formed of a closed transparent shell. Various methods have been used to contain the gas filled spheres between the parallel plates. In one method, spheres of varying sizes are tightly bunched and randomly distributed throughout a single layer, and sandwiched between the parallel plates. In a second method, spheres are embedded in a sheet of transparent dielectric material and that material is then sandwiched between the parallel plates. In a third method, a perforated sheet of electrically nonconductive material is sandwiched between the parallel plates with the gas filled spheres distributed in the perforations.

While each of the types of displays discussed above are based on different design concepts, the manufacturing approach used in their fabrication is generally the same. Conventionally, a batch fabrication process is used to manufacture these types of plasma panels. As is well known in the art, in a batch process individual component parts are fabricated separately, often in different facilities and by different manufacturers, and then brought together for final assembly where individual plasma panels are created one at a time. Batch processing has numerous shortcomings, such as, for example, the length of time necessary to produce a finished product. Long cycle times increase product cost and are undesirable for numerous additional reasons known in the art. For example, a sizeable quantity of substandard, defective, or useless fully or partially completed plasma panels may be produced during the period between detection of a defect or failure in one of the components and an effective correction of the defect or failure.

This is especially true of the first two types of displays discussed above; the first having no mechanical isolation of individual pixels, and the second with individual pixels mechanically isolated either by trenches formed in one parallel plate or by a perforated insulating layer sandwiched between two parallel plates. Due to the fact that plasma-forming gas is not isolated at the individual pixel/subpixel level, the fabrication process precludes the majority of individual component parts from being tested until the final display is assembled. Consequently, the display can only be tested after the two parallel plates are sealed together and the plasma-forming gas is filled inside the cavity between the two plates. If post production testing shows that any number of potential problems have occurred, (e.g. poor luminescence or no luminescence at specific pixels/subpixels) the entire display is discarded.

BRIEF SUMMARY OF THE INVENTION

Preferred embodiments of the present invention provide a light-emitting panel that may be used as a large-area radiation source, for energy modulation, for particle detection and as a flat-panel display. Gas-plasma panels are preferred for these applications due to their unique characteristics.

In one form, the light-emitting panel may be used as a large area radiation source. By configuring the light-emitting panel to emit ultraviolet (UV) light, the panel has application for curing, painting, and sterilization. With the addition of a white phosphor coating to convert the UV light to visible white light, the panel also has application as an illumination source.

In addition, the light-emitting panel may be used as a plasma-switched phase array by configuring the panel in at least one embodiment in a microwave transmission mode. The panel is configured in such a way that during ionization the plasma-forming gas creates a localized index of refraction change for the microwaves (although other wavelengths of light would work). The microwave beam from the panel can then be steered or directed in any desirable pattern by introducing at a localized area a phase shift and/or directing the microwaves out of a specific aperture in the panel Additionally, the light-emitting panel may be used for particle/photon detection. In this embodiment, the light-emitting panel is subjected to a potential that is just slightly below the write voltage required for ionization. When the device is subjected to outside energy at a specific position or location in the panel, that additional energy causes the plasma forming gas in the specific area to ionize, thereby providing a means of detecting outside energy.

Further, the light-emitting panel may be used in flat-panel displays. These displays can be manufactured very thin and lightweight, when compared to similar sized cathode ray tube (CRTs), making them ideally suited for home, office, theaters and billboards. In addition, these displays can be manufactured in large sizes and with sufficient resolution to accommodate high-definition television (HDTV). Gas-plasma panels do not suffer from electromagnetic distortions and are, therefore, suitable for applications strongly affected by magnetic fields, such as military applications, radar systems, railway stations and other underground systems.

According to one general embodiment of the present invention, a light-emitting panel is made from two substrates, wherein one of the substrates includes a plurality of sockets and wherein at least two electrodes are disposed. At least partially disposed in each socket is a micro-component, although more than one micro-component may be disposed therein. Each micro-component includes a shell at least partially filled with a gas or gas mixture capable of ionization. When a sufficiently large voltage is applied across the micro-component the gas or gas mixture ionizes forming plasma and emitting radiation.

In another embodiment of the present invention, at least two electrodes are adhered to the first substrate, the second substrate or any combination thereof.

In another embodiment, at least two electrodes are arranged so that voltage supplied to the electrodes causes at least one micro-component to emit radiation throughout the field of view of the light-emitting panel without the radiation crossing the electrodes.

In yet another embodiment, disposed in, or proximate to, each socket is at least one enhancement material.

Another preferred embodiment of the present invention is drawn to a web fabrication method for manufacturing light-emitting panels. In an embodiment, the web fabrication process includes providing a first substrate, disposing a plurality of micro-components on the first substrate, disposing a second substrate on the first substrate so that the at the micro-components are sandwiched between the first and second substrates, and dicing the first and second substrates to form individual light-emitting panels. In another embodiment, the web fabrication method includes the following process steps: a micro-component forming process; a micro-component coating process; a circuit and electrode printing process; a patterning process; a micro-component placement process; an electrode printing process; a second substrate application and alignment process; and a panel dicing process.

Other features, advantages, and embodiments of the invention are set forth in part in the description that follows, and in part, will be obvious from this description, or may be learned from the practice of the invention.

BRIEF DESCRIPTION OF THE DRAWINGS

The foregoing and other features and advantages of this invention will become more apparent by reference to the following detailed description of the invention taken in conjunction with the accompanying drawings.

FIG. 12 is a flowchart describing a web fabrication method for manufacturing light-emitting displays as described in an embodiment of the present invention.

DETAILED DESCRIPTION OF THE PREFERRED EMBODIMENTS OF THE INVENTION

As embodied and broadly described herein, the preferred embodiments of the present invention are directed to a novel light-emitting panel. In particular, preferred embodiments are directed to light-emitting panels and to a web fabrication process for manufacturing light-emitting panels.

Figure 1:
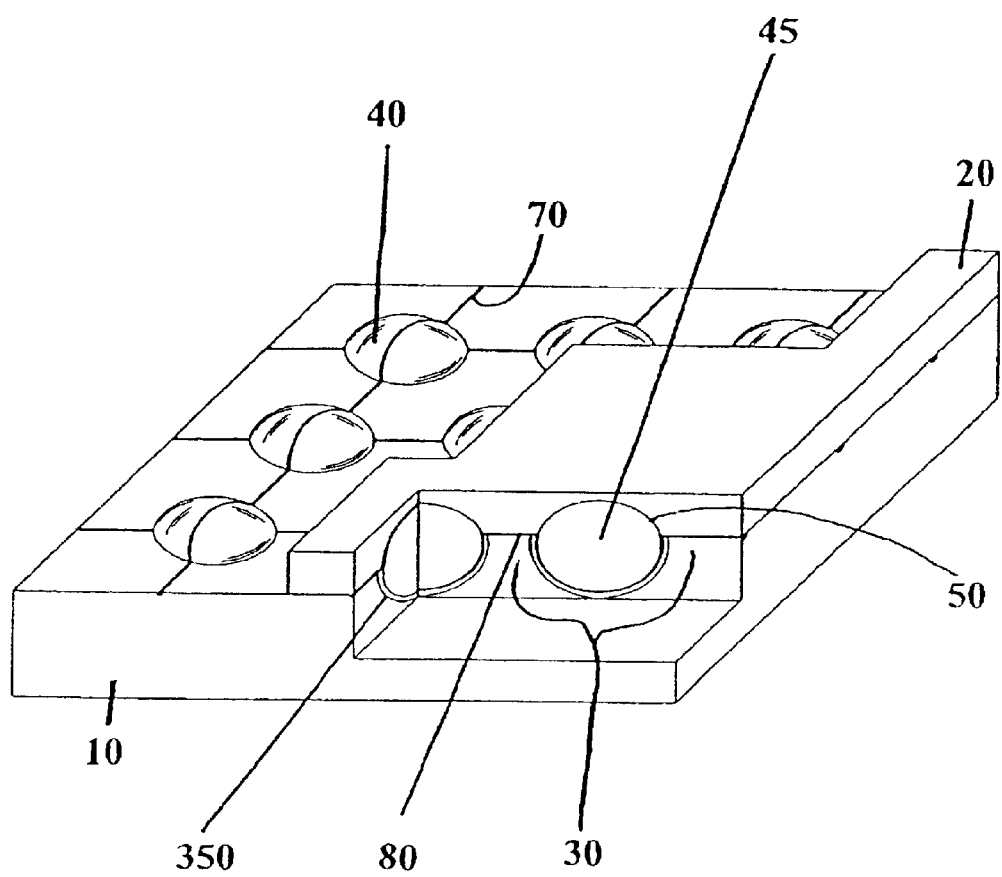
FIG. 1 depicts a portion of a light-emitting panel showing the basic socket structure of a socket formed from patterning a substrate, as disclosed in an embodiment of the present invention.
Figure 2:
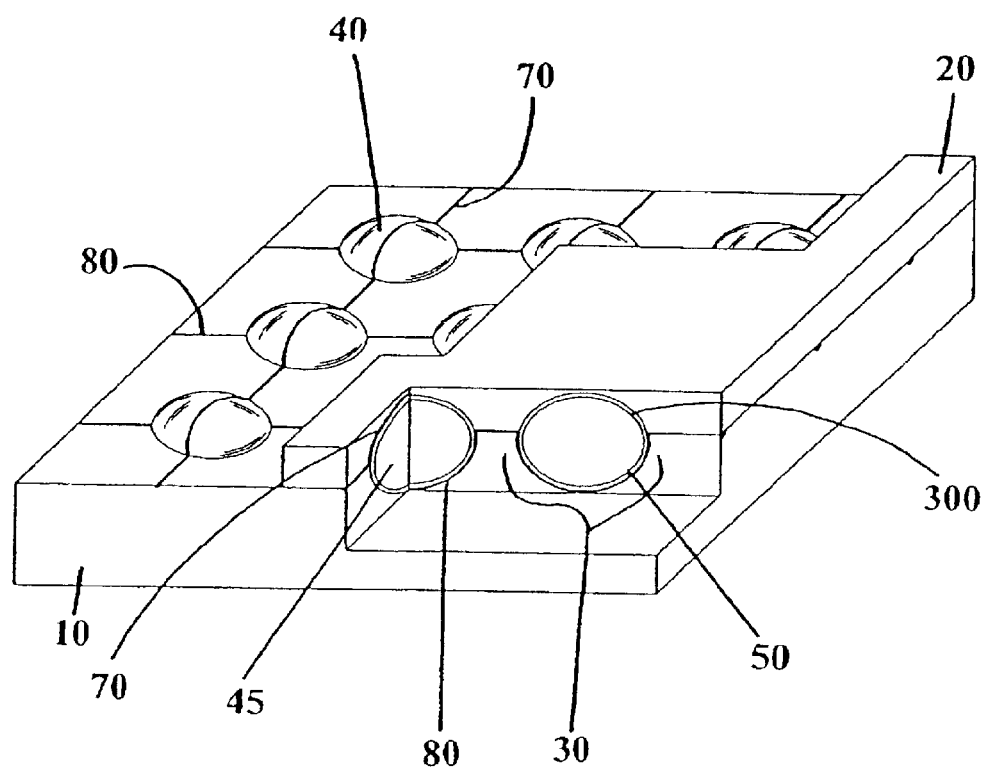
FIG. 2 depicts a portion of a light-emitting panel showing the basic socket structure of a socket formed from patterning a substrate, as disclosed in another embodiment of the present invention.
Figure 3A:
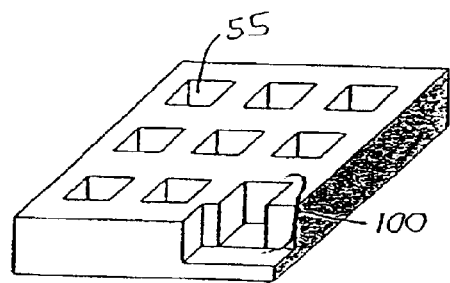
FIG. 3A shows an example of a cavity that has a cube shape.
Figure 3B:
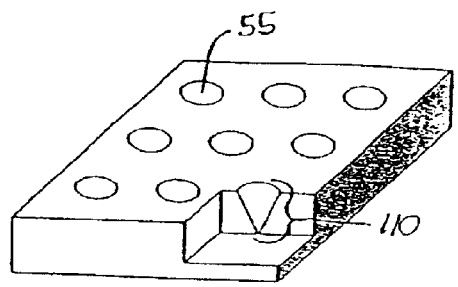
FIG. 3B shows an example of a cavity that has a cone shape.
Figure 3C:
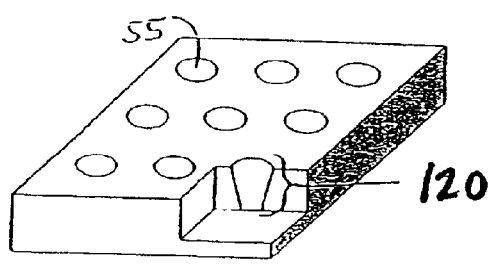
FIG. 3C shows an example of a cavity that has a conical frustum shape.
Figure 3D:
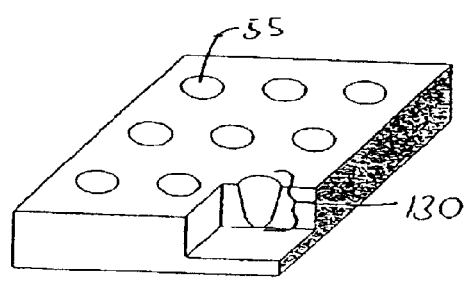
FIG. 3D shows an example of a cavity that has a paraboloid shape.
Figure 3E:
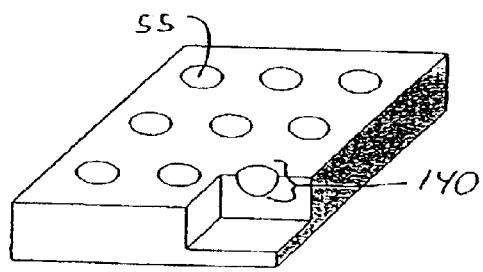
FIG. 3E shows an example of a cavity that has a spherical shape.
Figure 3F:
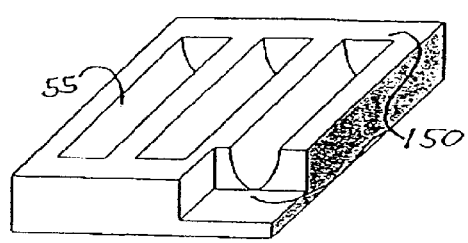
FIG. 3F shows an example of a cavity that has a cylindrical shape.
Figure 3G:
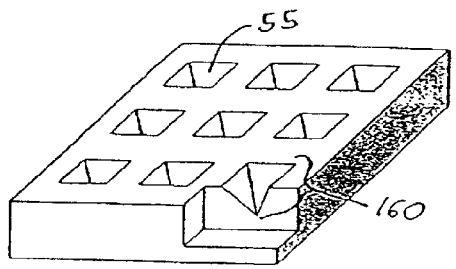
FIG. 3G shows an example of a cavity that has a pyramid shape.
Figure 3H:
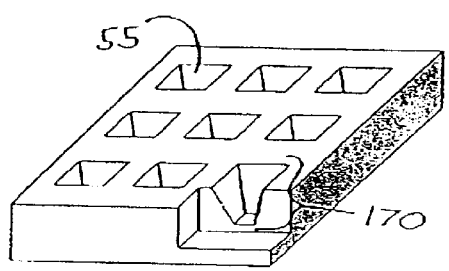
FIG. 3H shows an example of a cavity that has a pyramidal frustum shape.
Figure 3I:
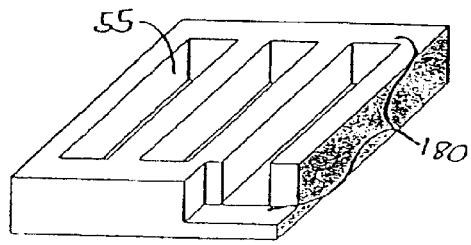
FIG. 3I shows an example of a cavity that has a parallelepiped shape.
Figure 3J:
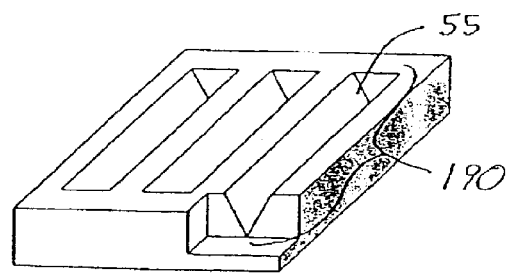
FIG. 3J shows an example of a cavity that has a prism shape.

FIGS. 1 and 2 show two embodiments of the present invention wherein a light-emitting panel includes a first substrate 10 and a second substrate 20. The first substrate 10 may be made from silicates, polypropylene, quartz, glass, any polymeric-based material or any material or combination of materials known to one skilled in the art. Similarly, second substrate 20 may be made from silicates, polypropylene, quartz, glass, any polymeric-based material or any material or combination of materials known to one skilled in the art. First substrate 10 and second substrate 20 may both be made from the same material or each of a different material. Additionally, the first and second substrate may be made of a material that dissipates heat from the light-emitting panel. In a preferred embodiment, each substrate is made from a material that is mechanically flexible.

The first substrate 10 includes a plurality of sockets 30. The sockets 30 may be disposed in any pattern, having uniform or non-uniform spacing between adjacent sockets. Patterns may include, but are not limited to, alphanumeric characters, symbols, icons, or pictures. Preferably, the sockets 30 are disposed in the first substrate 10 so that the distance between adjacent sockets 30 is approximately equal. Sockets 30 may also be disposed in groups such that the distance between one group of sockets and another group of sockets is approximately equal. This latter approach may be particularly relevant in color light-emitting panels, where each socket in each group of sockets may represent red, green and blue, respectively.

At least partially disposed in each socket 30 is at least one micro-component 40. Multiple micro-components may be disposed in a socket to provide increased luminosity and enhanced radiation transport efficiency. In a color light-emitting panel according to one embodiment of the present invention, a single socket supports three micro-components configured to emit red, green, and blue light, respectively. The micro-components 40 may be of any shape, including, but not limited to, spherical, cylindrical, and aspherical. In addition, it is contemplated that a micro-component 40 includes a micro-component placed or formed inside another structure, such as placing a spherical micro-component inside a cylindrical-shaped structure. In a color light-emitting panel according to an embodiment of the present invention, each cylindrical-shaped structure holds micro-components configured to emit a single color of visible light or multiple colors arranged red, green, blue, or in some other suitable color arrangement.

In another embodiment of the present invention, an adhesive or bonding agent is applied to each micro-component to assist in placing/holding a micro-component 40 or plurality of micro-components in a socket 30. In an alternative embodiment, an electrostatic charge is placed on each micro-component and an electrostatic field is applied to each micro-component to assist in the placement of a micro-component 40 or plurality of micro-components in a socket 30. Applying an electrostatic charge to the micro-components also helps avoid agglomeration among the plurality of micro-components. In one embodiment of the present invention, an electron gun is used to place an electrostatic charge on each micro-component and one electrode disposed proximate to each socket 30 is energized to provide the needed electrostatic field required to attract the electrostatically charged micro-component.

Alternatively, in order to assist placing/holding a micro-component 40 or plurality of micro-components in a socket 30, a socket 30 may contain a bonding agent or an adhesive. The bonding agent or adhesive may be applied to the inside of the socket 30 by differential stripping, lithographic process, sputtering, laser deposition, chemical deposition, vapor deposition, or deposition using ink jet technology. One skilled in the art will realize that other methods of coating the inside of the socket 30 may be used.

In its most basic form, each micro-component 40 includes a shell 50 filled with a plasma-forming gas or gas mixture 45. Any suitable gas or gas mixture 45 capable of ionization may be used as the plasma-forming gas, including, but not limited to, krypton, xenon, argon, neon, oxygen, helium, mercury, and mixtures thereof. In fact, any noble gas could be used as the plasma-forming gas, including, but not limited to, noble gases mixed with cesium or mercury. One skilled in the art would recognize other gasses or gas mixtures that could also be used. In a color display, according to another embodiment, the plasma-forming gas or gas mixture 45 is chosen so that during ionization the gas will irradiate a specific wavelength of light corresponding to a desired color. For example, neon-argon emits red light, xenon-oxygen emits green light, and krypton-neon emits blue light. While a plasma-forming gas or gas mixture 45 is used in a preferred embodiment, any other material capable of providing luminescence is also contemplated, such as an electro-luminescent material, organic light-emitting diodes (OLEDs), or an electro-phoretic material.

The shell 50 may be made from a wide assortment of materials, including, but not limited to, silicates, polypropylene, glass, any polymeric-based material, magnesium oxide and quartz and may be of any suitable size. The shell 50 may have a diameter ranging from micrometers to centimeters as measured across its minor axis, with virtually no limitation as to its size as measured across its major axis. For example, a cylindrical-shaped micro-component may be only 100 microns in diameter across its minor axis, but may be hundreds of meters long across its major axis. In a preferred embodiment, the outside diameter of the shell, as measured across its minor axis, is from 100 microns to 300 microns. In addition, the shell thickness may range from micrometers to millimeters, with a preferred thickness from 1 microns to 10 microns.

When a sufficiently large voltage is applied across the micro-component the gas or gas mixture ionizes forming plasma and emitting radiation. The potential required to initially ionize the gas or gas mixture inside the shell 50 is governed by Paschen's Law and is closely related to the pressure of the gas inside the shell. In the present invention, the gas pressure inside the shell 50 ranges from tens of torrs to several atmospheres. In a preferred embodiment, the gas pressure ranges from 100 torr to 700 torr. The size and shape of a micro-component 40 and the type and pressure of the plasma-forming gas contained therein, influence the performance and characteristics of the light-emitting panel and are selected to optimize the panel's efficiency of operation.

There are a variety of coatings 300 and dopants that may be added to a micro-component 40 that also influence the performance and characteristics of the light-emitting panel. The coatings 300 may be applied to the outside or inside of the shell 50, and may either partially or fully coat the shell 50. Types of outside coatings include, but are not limited to, coatings used to convert UV light to visible light (e.g. phosphor), coatings used as reflecting filters, and coatings used as band-gap filters. Types of inside coatings include, but are not limited to, coatings used to convert UV light to visible light (e.g. phosphor), coatings used to enhance secondary emissions and coatings used to prevent erosion. One skilled in the art will recognize that other coatings may also be used. The coatings 300 may be applied to the shell 50 by differential stripping, lithographic process, sputtering, laser deposition, chemical deposition, vapor deposition, or deposition using ink jet technology. One skilled in the art will realize that other methods of coating the inside and/or outside of the shell 50 may be used. Types of dopants include, but are not limited to, dopants used to convert UV light to visible light (e.g. phosphor), dopants used to enhance secondary emissions and dopants used to provide a conductive path through the shell 50. The dopants are added to the shell 50 by any suitable technique known to one skilled in the art, including ion implantation. It is contemplated that any combination of coatings and dopants may be added to a micro-component 40. Alternatively, or in combination with the coatings and dopants that may be added to a micro-component 40, a variety of coatings 350 may be coated on the inside of a socket 30. These coatings 350 include, but are not limited to, coatings used to convert UV light to visible light, coatings used as reflecting filters, and coatings used as band-gap filters.

In an embodiment of the present invention, when a micro-component is configured to emit UV light, the UV light is converted to visible light by at least partially coating the inside the shell 50 with phosphor, at least partially coating the outside of the shell 50 with phosphor, doping the shell 50 with phosphor and/or coating the inside of a socket 30 with phosphor. In a color panel, according to an embodiment of the present invention, colored phosphor is chosen so the visible light emitted from alternating micro-components is colored red, green and blue, respectively. By combining these primary colors at varying intensities, all colors can be formed. It is contemplated that other color combinations and arrangements may be used. In another embodiment for a color light-emitting panel, the UV light is converted to visible light by disposing a single colored phosphor on the micro-component 40 and/or on the inside of the socket 30. Colored filters may then be alternatingly applied over each socket 30 to convert the visible light to colored light of any suitable arrangement, for example red, green and blue. By coating all the micro-components with a single colored phosphor and then converting the visible light to colored light by using at least one filter applied over the top of each socket, micro-component placement is made less complicated and the light-emitting panel is more easily configurable.

To obtain an increase in luminosity and radiation transport efficiency, in an embodiment of the present invention, the shell 50 of each micro-component 40 is at least partially coated with a secondary emission enhancement material. Any low affinity material may be used including, but not limited to, magnesium oxide and thulium oxide. One skilled in the art would recognize that other materials will also provide secondary emission enhancement. In another embodiment of the present invention, the shell 50 is doped with a secondary emission enhancement material. It is contemplated that the doping of shell 50 with a secondary emission enhancement material may be in addition to coating the shell 50 with a secondary emission enhancement material. In this case, the secondary emission enhancement material used to coat the shell 50 and dope the shell 50 may be different.

In addition to, or in place of, doping the shell 50 with a secondary emission enhancement material, according to an embodiment of the present invention, the shell 50 is doped with a conductive material. Possible conductive materials include, but are not limited to silver, gold, platinum, and aluminum. Doping the shell 50 with a conductive material provides a direct conductive path to the gas or gas mixture contained in the shell and provides one possible means of achieving a DC light-emitting panel.

In another embodiment of the present invention, the shell 50 of the micro-component 40 is coated with a reflective material. An index matching material that matches the index of refraction of the reflective material is disposed so as to be in contact with at least a portion of the reflective material. The reflective coating and index matching material may be separate from, or in conjunction with, the phosphor coating and secondary emission enhancement coating of previous embodiments. The reflective coating is applied to the shell 50 in order to enhance radiation transport. By also disposing an index-matching material so as to be in contact with at least a portion of the reflective coating, a predetermined wavelength range of radiation is allowed to escape through the reflective coating at the interface between the reflective coating and the index-matching material. By forcing the radiation out of a micro-component through the interface area between the reflective coating and the index-matching material greater micro-component efficiency is achieved with an increase in luminosity. In an embodiment, the index matching material is coated directly over at least a portion of the reflective coating. In another embodiment, the index matching material is disposed on a material layer, or the like, that is brought in contact with the micro-component such that the index matching material is in contact with at least a portion of the reflective coating In another embodiment, the size of the interface is selected to achieve a specific field of view for the light-emitting panel.

A cavity 55 formed within and/or on the first substrate 10 provides the basic socket 30 structure. The cavity 55 may be any shape and size. As depicted in FIGS. 3A–3J, the shape of the cavity 55 may include, but is not limited to, a cube 100, a cone 110, a conical frustum 120, a paraboloid 130, spherical 140, cylindrical 150, a pyramid 160, a pyramidal frustum 170, a parallelepiped 180, or a prism 190.

Figure 4:
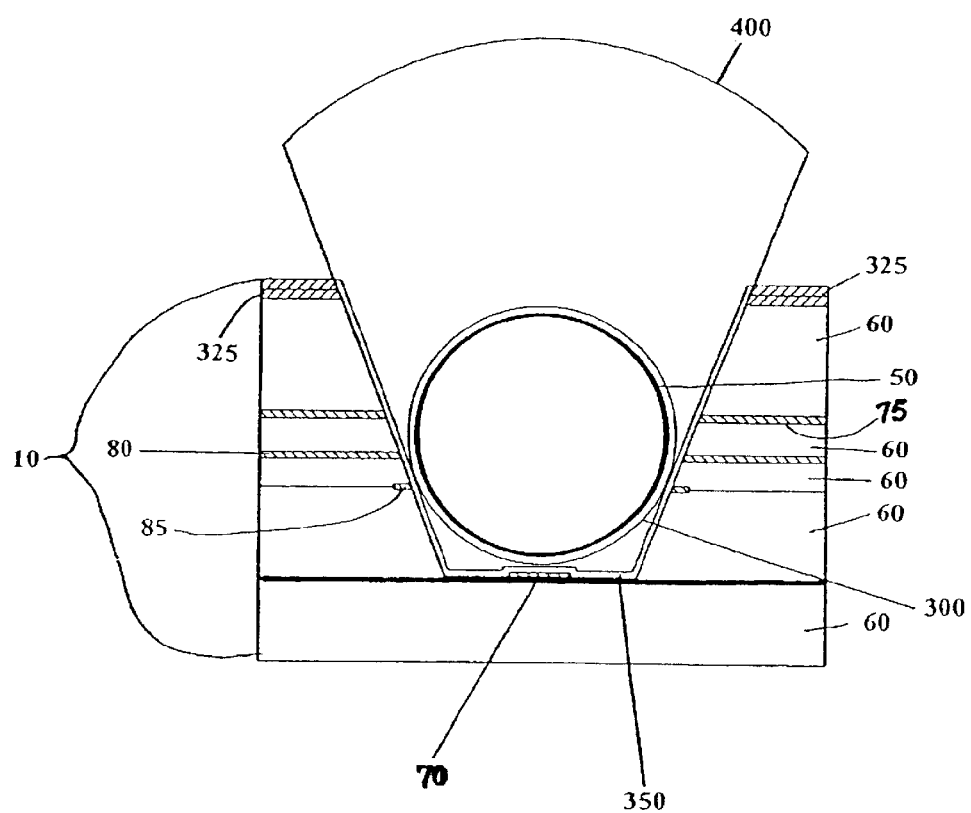
FIG. 4 shows the socket structure from a light-emitting panel of an embodiment of the present invention with a narrower field of view.
Figure 5:
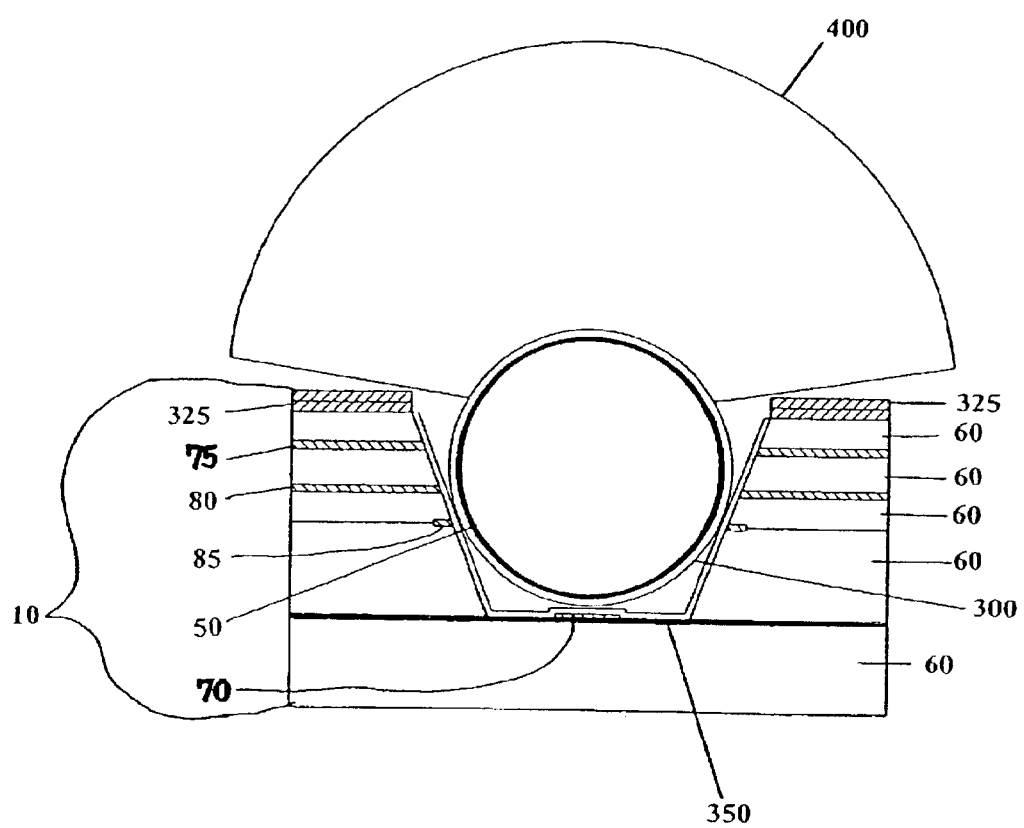
FIG. 5 shows the socket structure from a light-emitting panel of an embodiment of the present invention with a wider field of view.

The size and shape of the socket 30 influence the performance and characteristics of the light-emitting panel and are selected to optimize the panel's efficiency of operation. In addition, socket geometry may be selected based on the shape and size of the micro-component to optimize the surface contact between the micro-component and the socket and/or to ensure connectivity of the micro-component and any electrodes disposed within the socket. Further, the size and shape of the sockets 30 may be chosen to optimize photon generation and provide increased luminosity and radiation transport efficiency. As shown by example in FIGS. 4 and 5, the size and shape may be chosen to provide a field of view 400 with a specific angle θ, such that a micro-component 40 disposed in a deep socket 30 may provide more collimated light and hence a narrower viewing angle θ (FIG. 4), while a micro-component 40 disposed in a shallow socket 30 may provide a wider viewing angle θ (FIG. 5). That is to say, the cavity may be sized, for example, so that its depth subsumes a micro-component deposited in a socket, or it may be made shallow so that a micro-component is only partially disposed within a socket. Alternatively, in another embodiment of the present invention, the field of view 400 may be set to a specific angle θ by disposing on the second substrate at least one optical lens. The lens may cover the entire second substrate or, in the case of multiple optical lenses, arranged so as to be in register with each socket. In another embodiment, the optical lens or optical lenses are configurable to adjust the field of view of the light-emitting panel.

In an embodiment for a method of making a light-emitting panel including a plurality of sockets, a cavity 55 is formed, or patterned, in a substrate 10 to create a basic socket shape. The cavity may be formed in any suitable shape and size by any combination of physically, mechanically, thermally, electrically, optically, or chemically deforming the substrate. Disposed proximate to, and/or in, each socket may be a variety of enhancement materials 325. The enhancement materials 325 include, but are not limited to, anti-glare coatings, touch sensitive surfaces, contrast enhancement coatings, protective coatings, transistors, integrated-circuits, semiconductor devices, inductors, capacitors, resistors, control electronics, drive electronics, diodes, pulse-forming networks, pulse compressors, pulse transformers, and tuned-circuits.

In another embodiment of the present invention for a method of making a light-emitting panel including a plurality of sockets, a socket 30 is formed by disposing a plurality of material layers 60 to form a first substrate 10, disposing at least one electrode either directly on the first substrate 10, within the material layers or any combination thereof, and selectively removing a portion of the material layers 60 to create a cavity. The material layers 60 include any combination, in whole or in part, of dielectric materials, metals, and enhancement materials 325. The enhancement materials 325 include, but are not limited to, anti-glare coatings, touch sensitive surfaces, contrast enhancement coatings, protective coatings, transistors, integrated-circuits, semiconductor devices, inductors, capacitors, resistors, control electronics, drive electronics, diodes, pulse-forming networks, pulse compressors, pulse transformers, and tuned-circuits. The placement of the material layers 60 may be accomplished by any transfer process, photolithography, sputtering, laser deposition, chemical deposition, vapor deposition, or deposition using ink jet technology. One of general skill in the art will recognize other appropriate methods of disposing a plurality of material layers on a substrate. The cavity 55 may be formed in the material layers 60 by a variety of methods including, but not limited to, wet or dry etching, photolithography, laser heat treatment, thermal form, mechanical punch, embossing, stamping-out, drilling, electroforming or by dimpling.

In another embodiment of the present invention for a method of making a light-emitting panel including a plurality of sockets, a socket 30 is formed by patterning a cavity 55 in a first substrate 10, disposing a plurality of material layers 65 on the first substrate 10 so that the material layers 65 conform to the cavity 55, and disposing at least one electrode on the first substrate 10, within the material layers 65, or any combination thereof. The cavity may be formed in any suitable shape and size by any combination of physically, mechanically, thermally, electrically, optically, or chemically deforming the substrate. The material layers 60 include any combination, in whole or in part, of dielectric materials, metals, and enhancement materials 325. The enhancement materials 325 include, but are not limited to, anti-glare coatings, touch sensitive surfaces, contrast enhancement coatings, protective coatings, transistors, integrated-circuits, semiconductor devices, inductors, capacitors, resistors, control electronics, drive electronics, diodes, pulse-forming networks, pulse compressors, pulse transformers, and tuned-circuits. The placement of the material layers 60 may be accomplished by any transfer process, photolithography, sputtering, laser deposition, chemical deposition, vapor deposition, or deposition using ink jet technology. One of general skill in the art will recognize other appropriate methods of disposing a plurality of material layers on a substrate.

In another embodiment of the present invention for a method of making a light-emitting panel including a plurality of sockets, a socket 30 is formed by disposing a plurality of material layers 66 on a first substrate 10 and disposing at least one electrode on the first substrate 10, within the material layers 66, or any combination thereof. Each of the material layers includes a preformed aperture 56 that extends through the entire material layer. The apertures may be of the same size or may be of different sizes. The plurality of material layers 66 are disposed on the first substrate with the apertures in alignment thereby forming a cavity 55. The material layers 66 include any combination, in whole or in part, of dielectric materials, metals, and enhancement materials 325. The enhancement materials 325 include, but are not limited to, anti-glare coatings, touch sensitive surfaces, contrast enhancement coatings, protective coatings, transistors, integrated-circuits, semiconductor devices, inductors, capacitors, resistors, diodes, control electronics, drive electronics, pulse-forming networks, pulse compressors, pulse transformers, and tuned-circuits. The placement of the material layers 66 may be accomplished by any transfer process, photolithography, sputtering, laser deposition, chemical deposition, vapor deposition, or deposition using ink jet technology. One of general skill in the art will recognize other appropriate methods of disposing a plurality of material layers on a substrate.

In the above embodiments describing four different methods of making a socket in a light-emitting panel, disposed in, or proximate to, each socket may be at least one enhancement material. As stated above the enhancement material 325 may include, but is not limited to, anti-glare coatings, touch sensitive surfaces, contrast enhancement coatings, protective coatings, transistors, integrated-circuits, semiconductor devices, inductors, capacitors, resistors, control electronics, drive electronics, diodes, pulse-forming networks, pulse compressors, pulse transformers, and tuned-circuits. In a preferred embodiment of the present invention the enhancement materials may be disposed in, or proximate to each socket by any transfer process, photolithography, sputtering, laser deposition, chemical deposition, vapor deposition, deposition using ink jet technology, or mechanical means. In another embodiment of the present invention, a method for making a light-emitting panel includes disposing at least one electrical enhancement (e.g. the transistors, integrated-circuits, semiconductor devices, inductors, capacitors, resistors, control electronics, drive electronics, diodes, pulse-forming networks, pulse compressors, pulse transformers, and tuned-circuits), in, or proximate to, each socket by suspending the at least one electrical enhancement in a liquid and flowing the liquid across the first substrate. As the liquid flows across the substrate the at least one electrical enhancement will settle in each socket. It is contemplated that other substances or means may be use to move the electrical enhancements across the substrate. One such means may include, but is not limited to, using air to move the electrical enhancements across the substrate. In another embodiment of the present invention the socket is of a corresponding shape to the at least one electrical enhancement such that the at least one electrical enhancement self-aligns with the socket.

The electrical enhancements may be used in a light-emitting panel for a number of purposes including, but not limited to, lowering the voltage necessary to ionize the plasma-forming gas in a micro-component, lowering the voltage required to sustain/erase the ionization charge in a micro-component, increasing the luminosity and/or radiation transport efficiency of a micro-component, and augmenting the frequency at which a micro-component is lit. In addition, the electrical enhancements may be used in conjunction with the light-emitting panel driving circuitry to alter the power requirements necessary to drive the light-emitting panel. For example, a tuned-circuit may be used in conjunction with the driving circuitry to allow a DC power source to power an AC-type light-emitting panel. In an embodiment of the present invention, a controller is provided that is connected to the electrical enhancements and capable of controlling their operation. Having the ability to individual control the electrical enhancements at each pixel/subpixel provides a means by which the characteristics of individual micro-components may be altered/corrected after fabrication of the light-emitting panel. These characteristics include, but are not limited to, luminosity and the frequency at which a micro-component is lit. One skilled in the art will recognize other uses for electrical enhancements disposed in, or proximate to, each socket in a light-emitting panel.

The electrical potential necessary to energize a micro-component 40 is supplied via at least two electrodes. In a general embodiment of the present invention, a light-emitting panel includes a plurality of electrodes, wherein at least two electrodes are adhered to only the first substrate, only the second substrate or at least one electrode is adhered to each of the first substrate and the second substrate and wherein the electrodes are arranged so that voltage applied to the electrodes causes one or more micro-components to emit radiation. In another general embodiment, a light-emitting panel includes a plurality of electrodes, wherein at least two electrodes are arranged so that voltage supplied to the electrodes cause one or more micro-components to emit radiation throughout the field of view of the light-emitting panel without crossing either of the electrodes.

In an embodiment where the sockets 30 are patterned on the first substrate 10 so that the sockets are formed in the first substrate, at least two electrodes may be disposed on the first substrate 10, the second substrate 20, or any combination thereof. In exemplary embodiments as shown in FIGS. 1 and 2, a sustain electrode 70 is adhered on the second substrate 20 and an address electrode 80 is adhered on the first substrate 10. In a preferred embodiment, at least one electrode adhered to the first substrate 10 is at least partly disposed within the socket (FIGS. 1 and 2).

Figure 6A:
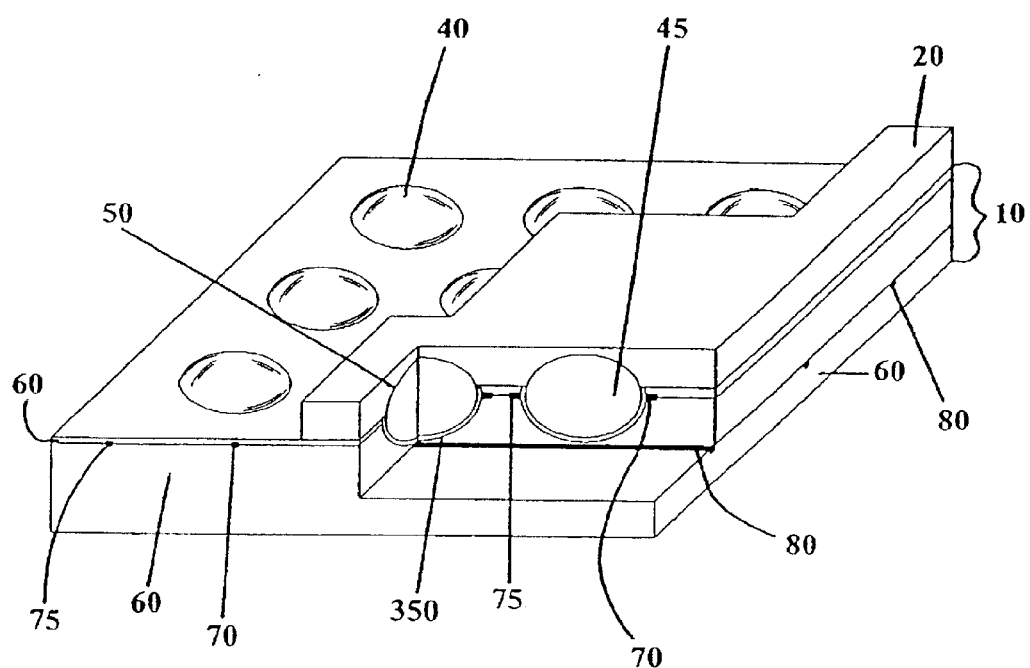
FIG. 6A depicts a portion of a light-emitting panel showing the basic socket structure of a socket formed from disposing a plurality of material layers and then selectively removing a portion of the material layers with the electrodes having a co-planar configuration.
Figure 6B:
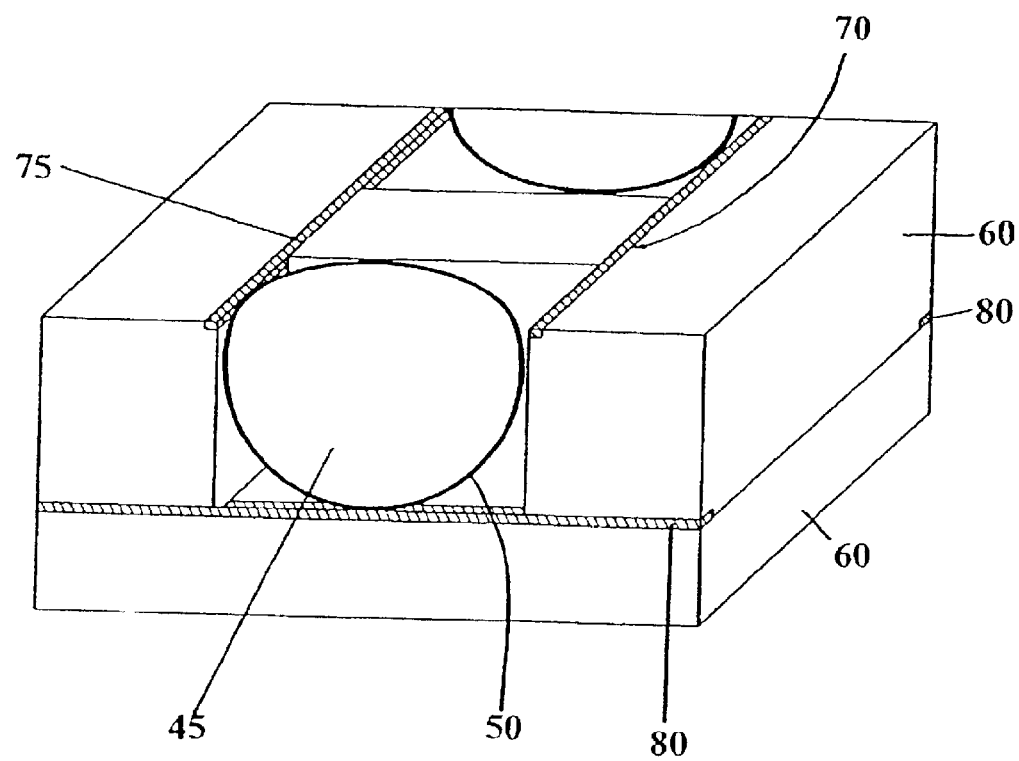
FIG. 6B is a cut-away of FIG. 6A showing in more detail the co-planar sustaining electrodes.
Figure 7A:
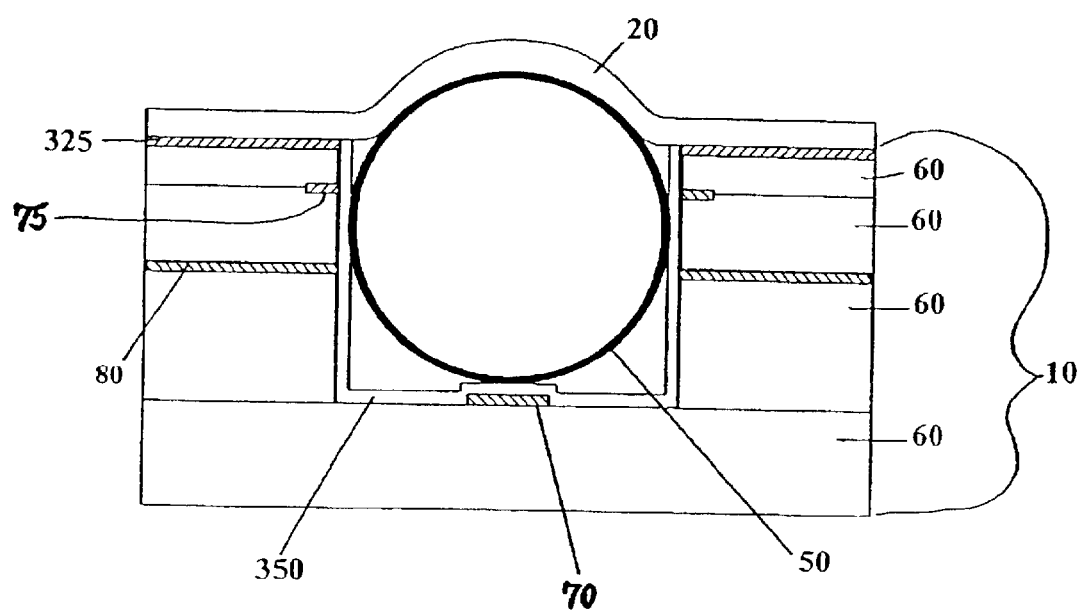
FIG. 7A depicts a portion of a light-emitting panel showing the basic socket structure of a socket formed from disposing a plurality of material layers and then selectively removing a portion of the material layers with the electrodes having a mid-plane configuration.
Figure 7B:
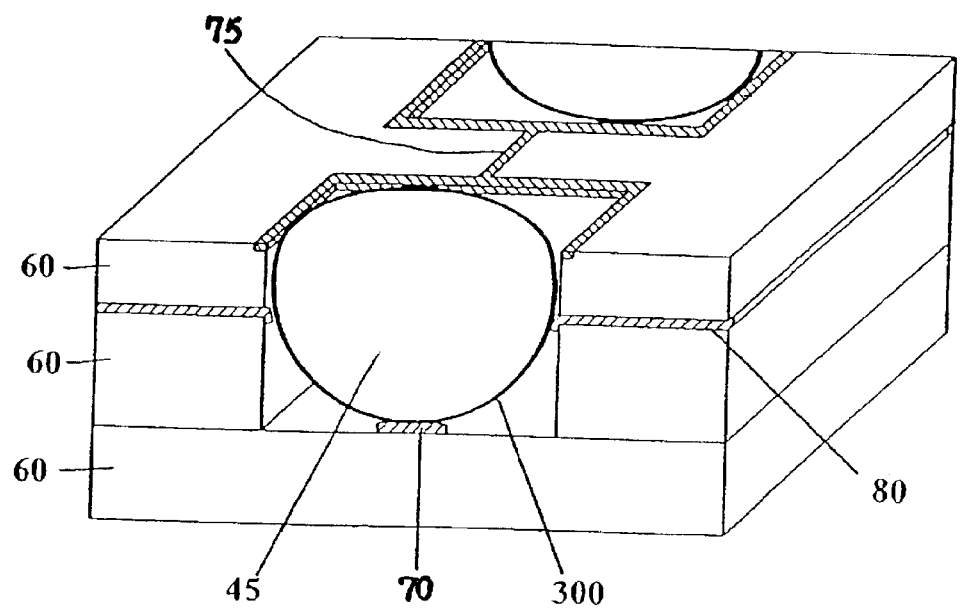
FIG. 7B is a cut-away of FIG. 7A showing in more detail the uppermost sustain electrode.
Figure 8:
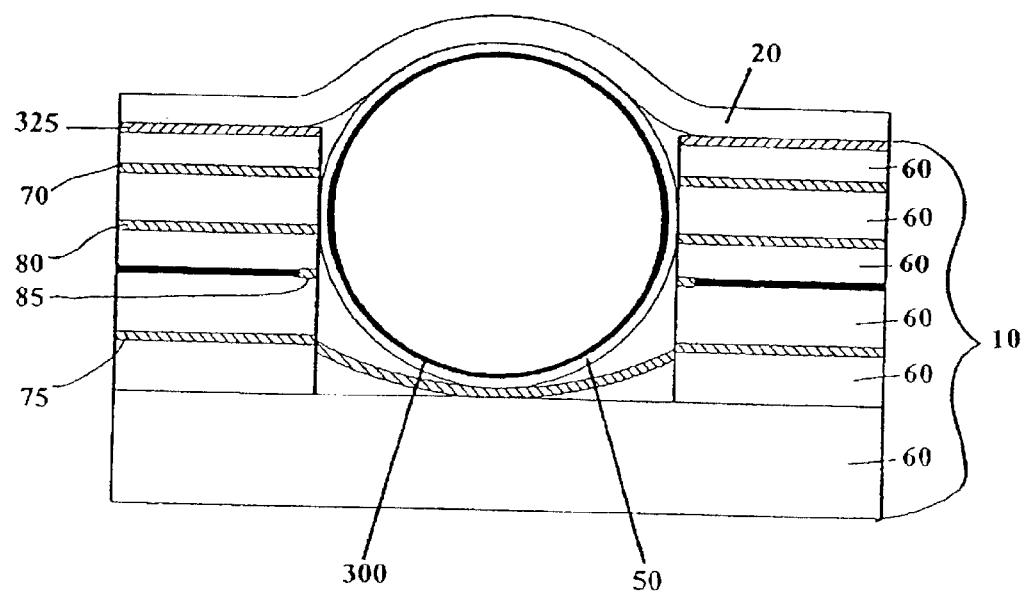
FIG. 8 depicts a portion of a light-emitting panel showing the basic socket structure of a socket formed from disposing a plurality of material layers and then selectively removing a portion of the material layers with the electrodes having an configuration with two sustain and two address electrodes, where the address electrodes are between the two sustain electrodes.

In an embodiment where the first substrate 10 includes a plurality of material layers 60 and the sockets 30 are formed within the material layers, at least two electrodes may be disposed on the first substrate 10, disposed within the material layers 60, disposed on the second substrate 20, or any combination thereof. In one embodiment, as shown in FIG. 6A, a first address electrode 80 is disposed within the material layers 60, a first sustain electrode 70 is disposed within the material layers 60, and a second sustain electrode 75 is disposed within the material layers 60, such that the first sustain electrode and the second sustain electrode are in a co-planar configuration. FIG. 6B is a cut-away of FIG. 6A showing the arrangement of the co-planar sustain electrodes 70 and 75. In another embodiment, as shown in FIG. 7A, a first sustain electrode 70 is disposed on the first substrate 10, a first address electrode 80 is disposed within the material layers 60, and a second sustain electrode 75 is disposed within the material layers 60, such that the first address electrode is located between the first sustain electrode and the second sustain electrode in a mid-plane configuration. FIG. 7B is a cut-away of FIG. 7A showing the first sustain electrode 70. As seen in FIG. 8, in a preferred embodiment of the present invention, a first sustain electrode 70 is disposed within the material layers 60, a first address electrode 80 is disposed within the material layers 60, a second address electrode 85 is disposed within the material layers 60, and a second sustain electrode 75 is disposed within the material layers 60, such that the first address electrode and the second address electrode are located between the first sustain electrode and the second sustain electrode.

Figure 9:
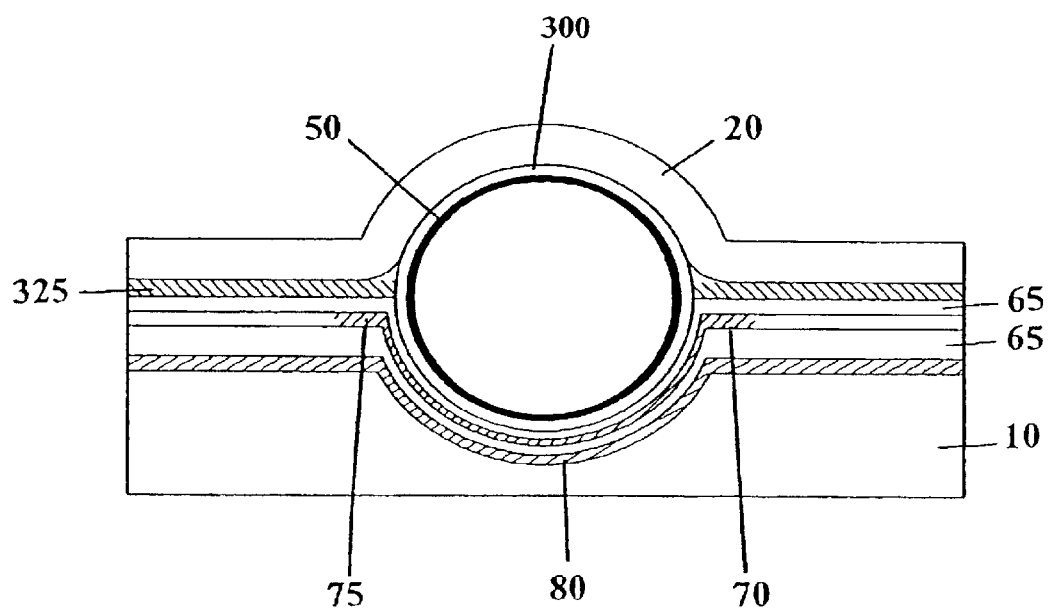
FIG. 9 depicts a portion of a light-emitting panel showing the basic socket structure of a socket formed from patterning a substrate and then disposing a plurality of material layers on the substrate so that the material layers conform to the shape of the cavity with the electrodes having a co-planar configuration.
Figure 10:
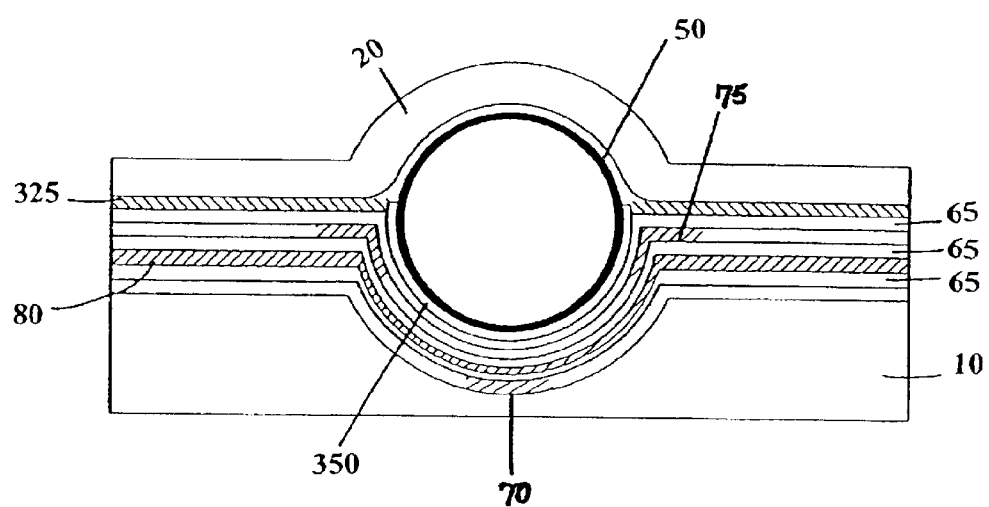
FIG. 10 depicts a portion of a light-emitting panel showing the basic socket structure of a socket formed from patterning a substrate and then disposing a plurality of material layers on the substrate so that the material layers conform to the shape of the cavity with the electrodes having a mid-plane configuration.
Figure 11:
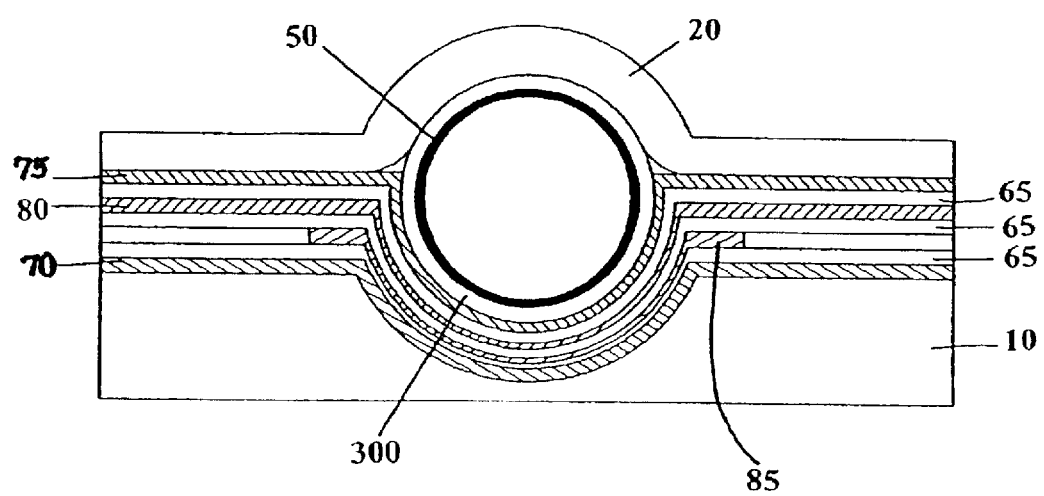
FIG. 11 depicts a portion of a light-emitting panel showing the basic socket structure of a socket formed from patterning a substrate and then disposing a plurality of material layers on the substrate so that the material layers conform to the shape of the cavity with the electrodes having an configuration with two sustain and two address electrodes, where the address electrodes are between the two sustain electrodes.

In an embodiment where a cavity 55 is patterned on the first substrate 10 and a plurality of material layers 65 are disposed on the first substrate 10 so that the material layers conform to the cavity 55, at least two electrodes may be disposed on the first substrate 10, at least partially disposed within the material layers 65, disposed on the second substrate 20, or any combination thereof. In one embodiment, as shown in FIG. 9, a first address electrode 80 is disposed on the first substrate 10, a first sustain electrode 70 is disposed within the material layers 65, and a second sustain electrode 75 is disposed within the material layers 65, such that the first sustain electrode and the second sustain electrode are in a co-planar configuration. In another embodiment, as shown in FIG. 10, a first sustain electrode 70 is disposed on the first substrate 10, a first address electrode 80 is disposed within the material layers 65, and a second sustain electrode 75 is disposed within the material layers 65, such that the first address electrode is located between the first sustain electrode and the second sustain electrode in a mid-plane configuration. As seen in FIG. 11, in a preferred embodiment of the present invention, a first sustain electrode 70 is disposed on the first substrate 10, a first address electrode 80 is disposed within the material layers 65, a second address electrode 85 is disposed within the material layers 65, and a second sustain electrode 75 is disposed within the material layers 65, such that the first address electrode and the second address electrode are located between the first sustain electrode and the second sustain electrode.

Figure 15:
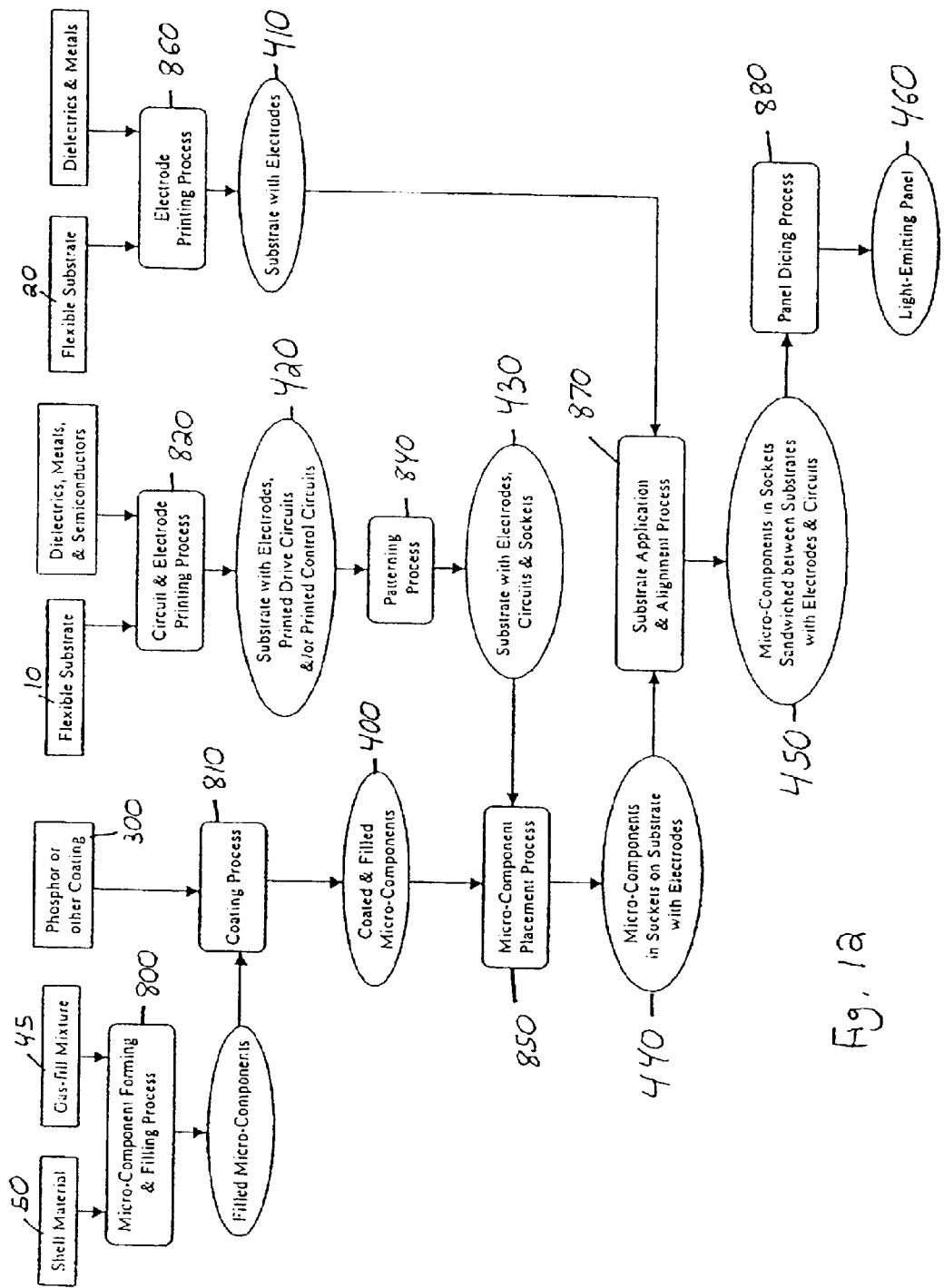
FIG. 15 shows an exploded view of a portion of a light-emitting panel showing the basic socket structure of a socket formed by disposing a plurality of material layers with aligned apertures on a substrate with the electrodes having a mid-plane configuration.
Figure 14:
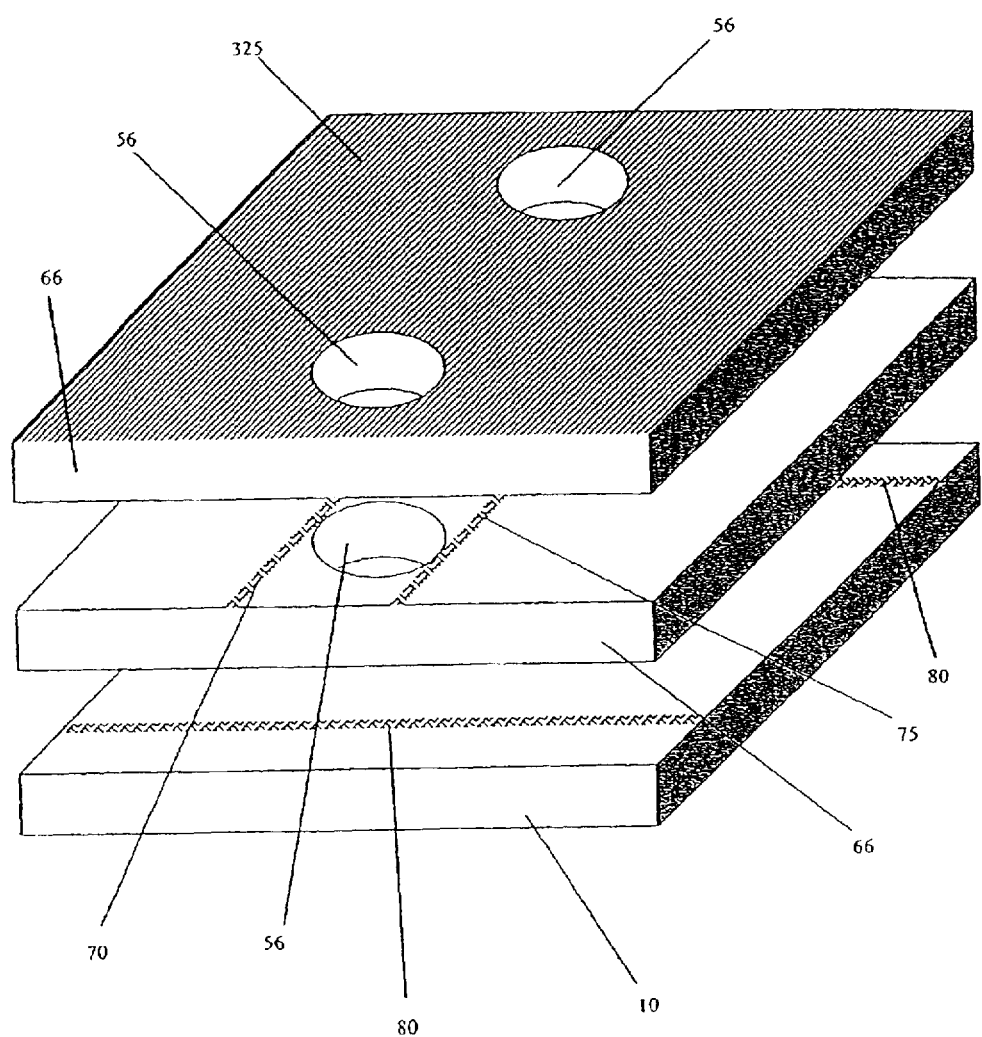
FIG. 14 shows an exploded view of a portion of a light-emitting panel showing the basic socket structure of a socket formed by disposing a plurality of material layers with aligned apertures on a substrate with the electrodes having a co-planar configuration.
Figure 15:
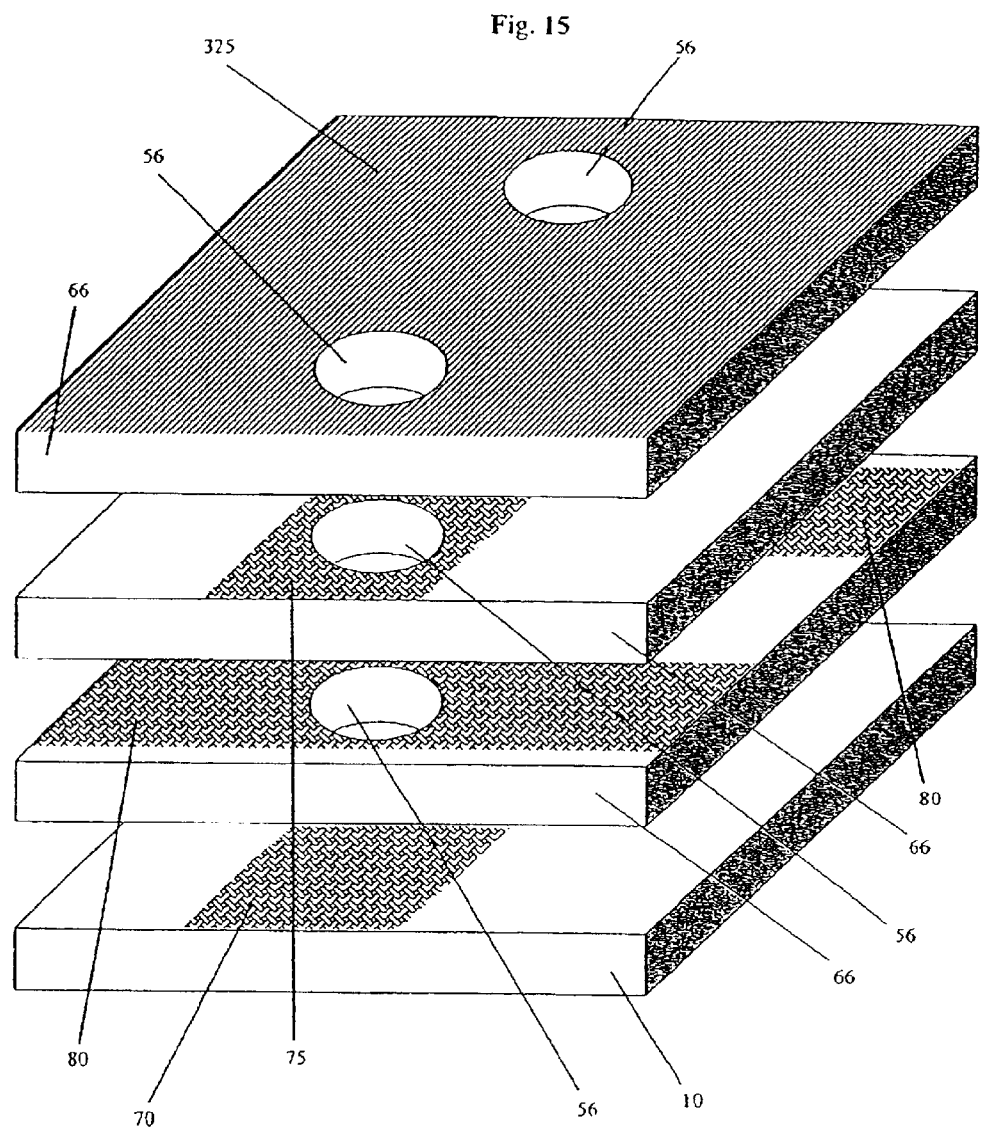
Figure 16:
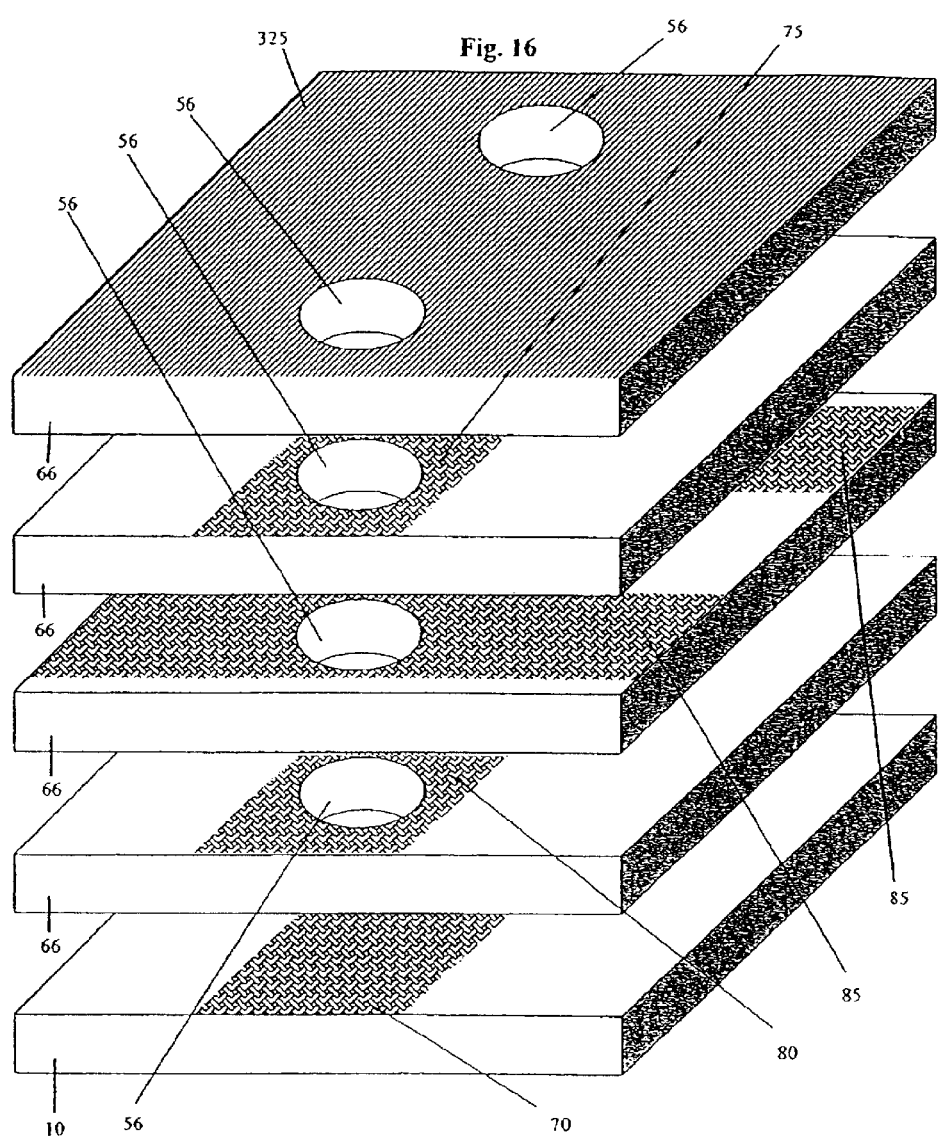
FIG. 16 shows an exploded view of a portion of a light-emitting panel showing the basic socket structure of a socket formed by disposing a plurality of material layers with aligned apertures on a substrate with electrodes having a configuration with two sustain and two address electrodes, where the address electrodes are between the two sustain electrodes.

In an embodiment where a plurality of material layers 66 with aligned apertures 56 are disposed on a first substrate 10 thereby creating the cavities 55, at least two electrodes may be disposed on the first substrate 10, at least partially disposed within the material layers 65, disposed on the second substrate 20, or any combination thereof. In one embodiment, as shown in FIG. 14, a first address electrode 80 is disposed on the first substrate 10, a first sustain electrode 70 is disposed within the material layers 66, and a second sustain electrode 75 is disposed within the material layers 66, such that the first sustain electrode and the second sustain electrode are in a co-planar configuration. In another embodiment, as shown in FIG. 15, a first sustain electrode 70 is disposed on the first substrate 10, a first address electrode 80 is disposed within the material layers 66, and a second sustain electrode 75 is disposed within the material layers 66, such that the first address electrode is located between the first sustain electrode and the second sustain electrode in a mid-plane configuration. As seen in FIG. 16, in a preferred embodiment of the present invention, a first sustain electrode 70 is disposed on the first substrate 10, a first address electrode 80 is disposed within the material layers 66, a second address electrode 85 is disposed within the material layers 66, and a second sustain electrode 75 is disposed within the material layers 66, such that the first address electrode and the second address electrode are located between the first sustain electrode and the second sustain electrode.

The specification, above, has described, among other things, various components of a light-emitting panel and methodologies to make those components and to make a light-emitting panel. In an embodiment of the present invention, it is contemplated that those components may be manufactured and those methods for making may be accomplished as part of web fabrication process for manufacturing light-emitting panels. In another embodiment of the present invention, a web fabrication process for manufacturing light-emitting panels includes the steps of providing a first substrate, disposing micro-components on the first substrate, disposing a second substrate on the first substrate so that the micro-components are sandwiched between the first and second substrates, and dicing the first and second substrate "sandwich" to form individual light-emitting panels. In another embodiment, the first and second substrates are provided as rolls of material. A plurality of sockets may either be preformed on the first substrate or may be formed in and/or on the first substrate as part of the web fabrication process. Likewise, the first and second substrates may be preformed so that the fist substrate, the second substrate or both substrates include a plurality of electrodes. Alternatively, a plurality of electrodes may be disposed on or within the first substrate, on or within the second substrate, or on and within both the first substrate and second substrate as part of the web fabrication process. It should be noted that where suitable, fabrication steps may be performed in any order. It should also be noted that the micro-components may be preformed or may be formed as part of the web fabrication process. In another embodiment, the web fabrication process is performed as a continuous high-speed inline process with the ability to manufacture light-emitting panels at a rate faster than light-emitting panels manufactured as part of batch process.

Figure 13:
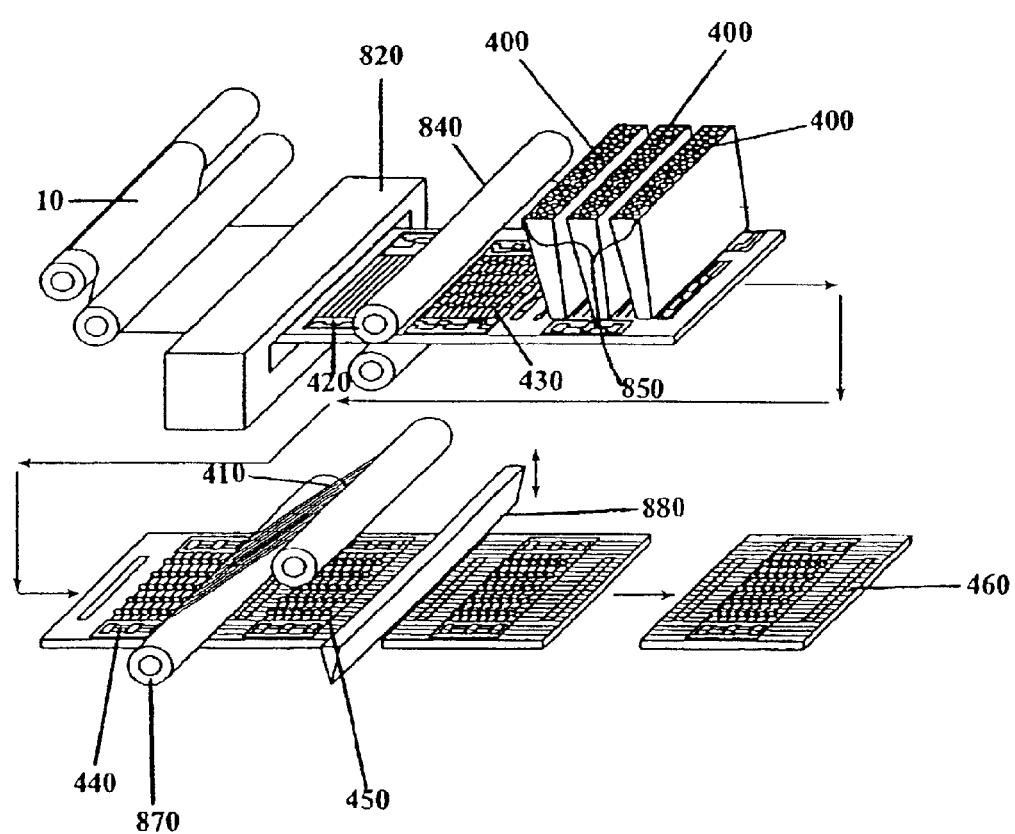
FIG. 13 is a graphical representation of a web fabrication method for manufacturing light-emitting panels as described in an embodiment of the present invention.

As shown in FIGS. 12 and 13, in an embodiment of the present invention, the web fabrication process includes the following process steps: a micro-component forming process 800 for forming the micro-component shells and filling the micro-components with plasma-forming gas; a micro-component coating process 810 for coating the micro-components with phosphor or any other suitable coatings and producing a plurality of coated and filled micro-components 400; a circuit and electrode printing process 820 for printing at least one electrode and any needed driving and control circuitry on a first substrate 420; a patterning process 840 for patterning a plurality of cavities on a first substrate to form a plurality of sockets 430; a micro-component placement process 850 for properly placing at least one micro-component in each socket 430; an electrode printing process 860 for printing, if required, at least one electrode on a second substrate 410; a second substrate application and alignment process 870 for aligning the second substrate over the first substrate 440 so that the micro-components are sandwiched between the first substrate and the second substrate 450; and a panel dicing process 880 for dicing the first and second substrates 450 to form individual light-emitting panels 460.

Figure 17:
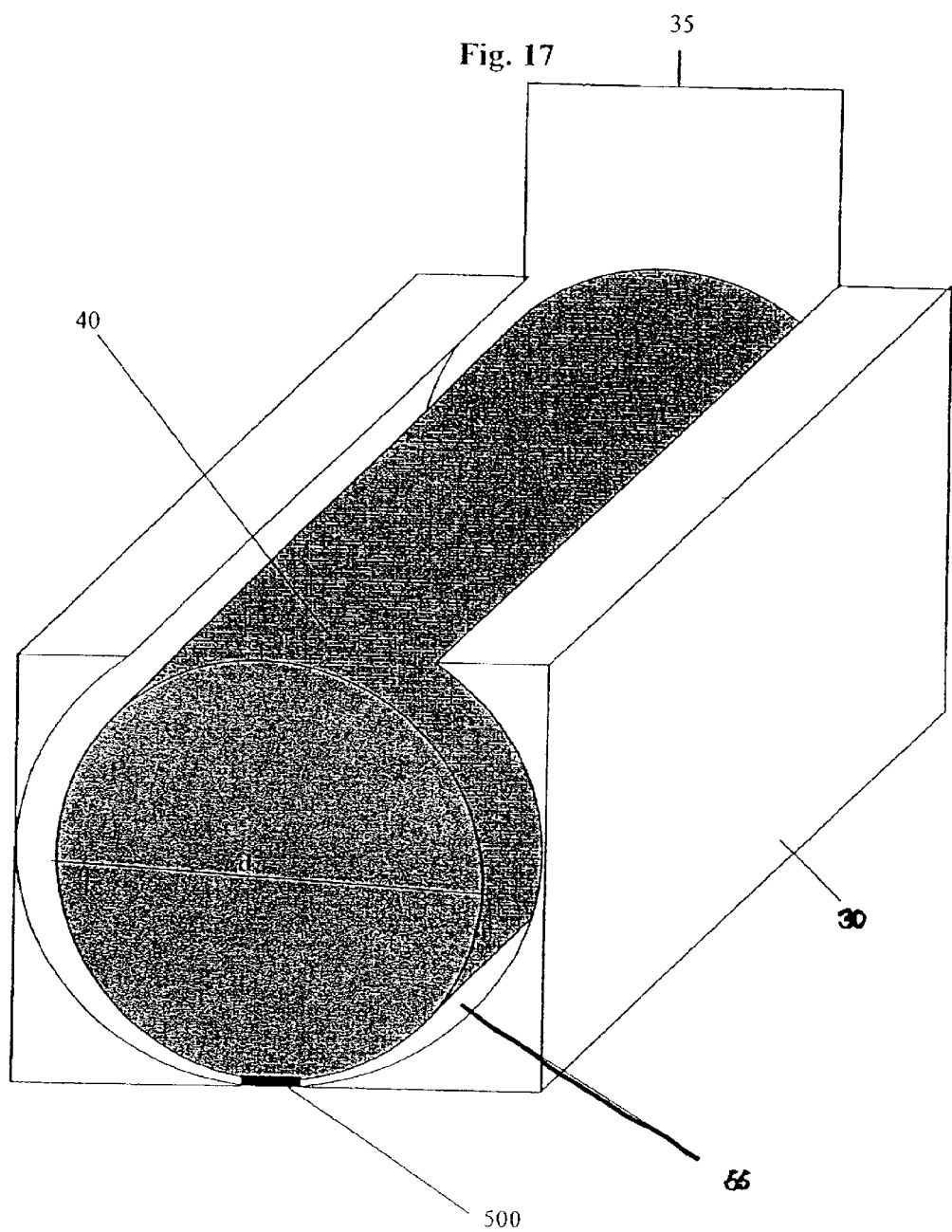
FIG. 17 shows a portion of a socket of an embodiment of the present invention where the micro-component and the cavity are formed as a type of male-female connector.

In another embodiment of the present invention as shown in FIG. 17, the socket 30 may be formed as a type of male-female connector with a male micro-component 40 and a female cavity 55. The male micro-component 40 and female cavity 55 are formed to have complimentary shapes. As shown in FIG. 12, as an example, both the cavity and micro-component have complimentary cylindrical shapes. The opening 35 of the female cavity is formed such that the opening is smaller than the diameter d of the male micro-component. The larger diameter male micro-component can be forced through the smaller opening of the female cavity 55 so that the male micro-component 40 is locked/held in the cavity and automatically aligned in the socket with respect to at least one electrode 500 disposed therein. This arrangement provides an added degree of flexibility for micro-component placement. In another embodiment, this socket structure provides a means by which cylindrical micro-components may be fed through the sockets on a row-by-row basis or in the case of a single long cylindrical micro-component (although other shapes would work equally well) fed/woven throughout the entire light-emitting panel.

Figure 18:
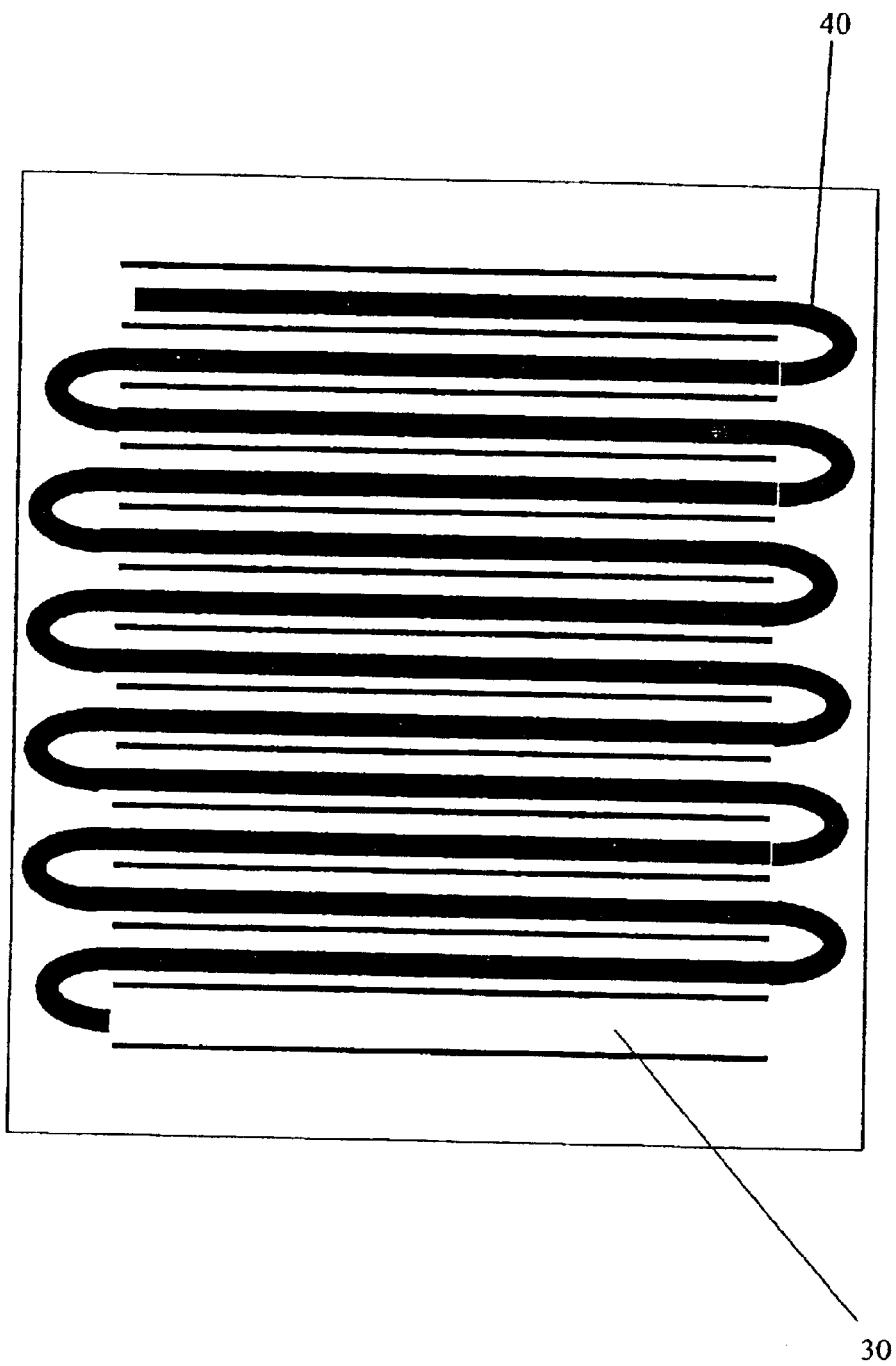
FIG. 18 shows a top down view of a portion of a light-emitting panel showing a method for making a light-emitting panel by weaving a single micro-component through the entire light-emitting panel.
Figure 19:
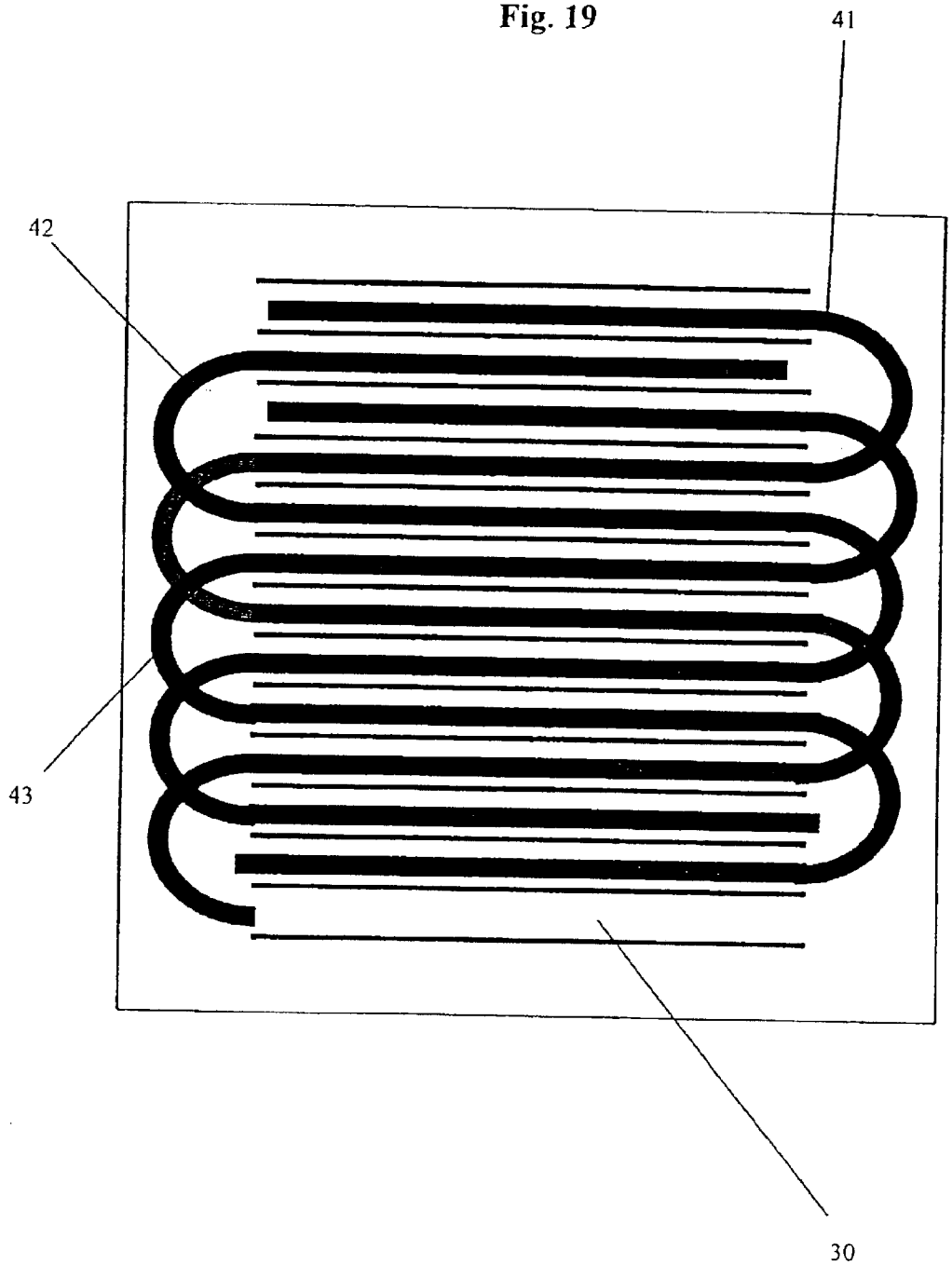
FIG. 19 shows a top down view of a portion of a color light-emitting panel showing a method for making a color light-emitting panel by weaving multiple micro-components through the entire light-emitting panel.

In another embodiment of the present invention, as shown in FIG. 18, a method for making a light-emitting panel includes weaving a single micro-component 40 through each socket 30 for the entire length of the light-emitting panel. Any socket 30 formed in the shape of a channel will work equally well in this embodiment. In a preferred embodiment, however, the socket illustrates in FIG. 17, and described above, is used. As the single micro-component 40 is being woven/fed through the socket channels and as the single micro-component reaches the end of a channel, it is contemplated in an embodiment that the micro-component 40 will be heat treated so as to allow the micro-component 40 to bend around the end of the socket channel. In another embodiment, as shown in FIG. 19, a method for making a color light-emitting panel includes weaving a plurality of micro-components 40, each configured to emit a specific color of visible light, alternatingly through the entire light-emitting panel. For example, as shown in FIG. 19, a red micro-component 41, a green micro-component 42 and a blue micro-component 43 are woven/fed through the socket channels. Alternatively, a color light-emitting panel may be made by alternatingly coating the inside of each socket channel with a specific color phosphor or other UV conversion material, and then weaving/feeding a plurality of micro-components through the socket channels for the entire length of the light-emitting panel.

Other embodiments and uses of the present invention will be apparent to those skilled in the art from consideration of this application and practice of the invention disclosed herein. The present description and examples should be considered exemplary only, with the true scope and spirit of the invention being indicated by the following claims. As will be understood by those of ordinary skill in the art, variations and modifications of each of the disclosed embodiments, including combinations thereof, can be made within the scope of this invention as defined by the following claims.

What is claimed is:

1. A light-emitting panel comprising:
   a first substrate, wherein the first substrate comprises a plurality of sockets; a plurality of micro-components, wherein each micro-component comprises a shell at least partially filled with a plasma-forming gas and wherein at least one micro-component of the plurality of micro-components is at least partially disposed in each socket;

a second substrate, wherein the second substrate is opposed to the first substrate such that the at least one micro-component is sandwiched between the first substrate and the second substrate and further wherein the second substrate comprises a plurality of lenses configurable to adjust a field of view of the light-emitting panel wherein a ratio of lenses to sockets is 1:1; and a plurality of electrodes, wherein at least two electrodes of the plurality of electrodes are adhered to only the first substrate, only the second substrate, or at least one electrode is adhered to each of the first substrate and the second substrate and wherein the at least two electrodes are arranged so that voltage supplied to the at least two electrodes causes one or more micro-components to emit radiation.

2. The light-emitting panel of claim 1, wherein the second substrate comprises at least one filter.

3. The light-emitting panel of claim 2, wherein the plurality of micro-components are configured to emit ultraviolet radiation, wherein each micro-component is coated with phosphor to convert the ultraviolet radiation to visible light, and wherein the at least one filter changes the visible light passing through the filter to visible light of a specific color.

4. The light-emitting panel of claim 1, wherein the emitted radiation is ultraviolet radiation, and further wherein each of the plurality of sockets is at least partially coated with phosphor in order to convert the ultraviolet radiation into red, green, or blue visible light.

5. A light-emitting panel, comprising:

a first substrate, wherein the first substrate comprises a plurality of sockets; a plurality of micro-components, wherein each micro-component comprises a shell at least partially filled with a plasma-forming gas and wherein at least one micro-component of the plurality of micro-components is at least partially disposed in each socket;

a second substrate, wherein the second substrate is opposed to the first substrate such that the at least one micro-component is sandwiched between the first substrate and the second substrate; and a plurality of electrodes, wherein at least two electrodes of the plurality of electrodes are arranged so that voltage supplied to the at least two electrodes causes one or more micro-components to emit radiation throughout the field of view of the light-emitting panel without crossing the at least two electrodes.

6. The light-emitting panel of claim 5, wherein the first substrate dissipates heat from the light-emitting panel.

7. The light-emitting display of claim 5, wherein each socket includes at least one enhancement material is disposed in or proximate to each socket and wherein the at least one enhancement material is selected from a group consisting of transistors, integrated-circuits, semiconductor devices, inductors, capacitors, resistors, control electronics, drive electronics, diodes, pulse-forming networks, pulse compressors, pulse transformers, and tuned-circuits.

8. The light-emitting display of claim 7, wherein the at least one enhancement material self-aligns in each socket.

9. The light-emitting display of claim 7, further comprising a controller, wherein the controller selectively controls the operation of the at least one enhancement material to adjust at least one characteristic of the micro-component.

10. The colored light-emitting panel of claim 5, wherein the second substrate is formed of a heat dissipating material.

11. The colored light-emitting panel of claim 5, wherein the plurality of sockets is disposed in uniformly spaced pattern on the first substrate.

12. The light-emitting panel of claim 5, wherein the plasma-forming gas is selected from the group consisting of neon-argon, xenon-oxygen, and krypton-neon.

13. The light-emitting panel of claim 5, further comprising colored filters applied over each of the plurality of sockets for converting the emitted radiation from each of the plurality of micro-components into red, green, or blue visible light.

14. The light-emitting panel of claim 5, wherein the emitted radiation is ultraviolet radiation, and further wherein each of the plurality of micro-components is at least partially coated with phosphor in order to convert the ultraviolet radiation into red, green, or blue visible light.

15. The light-emitting panel of claim 5, wherein the emitted radiation is ultraviolet radiation, and further wherein each of the plurality of sockets is at least partially coated with phosphor in order to convert the ultraviolet radiation into red, green, or blue visible light.

16. The light-emitting panel of claim 5, further comprising means for selecting a particular field of view for the emitted radiation from the light-emitting panel.

17. The light-emitting panel of claim 16, wherein the means is a single lens.

18. The colored light-emitting panel of claim 16, wherein the means is a plurality of lenses, wherein the ratio of lenses to sockets is 1:1.

19. A colored light-emitting panel comprising:

a first substrate comprising a plurality of sockets;

a plurality of micro-components, wherein each of the plurality of micro-components is at least partially filled with an ionizable gas and is configured to emit radiation resulting in visible light having one of the following colors red, green, and blue being emitted from the light-emitting panel, and further wherein at least one micro-component of the plurality of micro-components is at least partially disposed in each of the plurality of sockets;

a second substrate, wherein the second substrate is opposed to the first substrate such that the plurality of micro-components are sandwiched between the first substrate and the second substrate; and means for applying a voltage across each of the plurality of micro-components to ionize the ionizable gas and cause each of the plurality of micro-components to emit the radiation throughout a field of view of the light-emitting panel without crossing the means for applying a voltage across each of the plurality of micro-components.

20. The colored light-emitting panel of claim 19, wherein at least one of the first and second substrates are formed of a heat dissipating material.

21. The colored light-emitting panel of claim 19, wherein the plurality of sockets is disposed in uniformly spaced pattern on the first substrate.

22. The colored light-emitting panel of claim 19, wherein the ionizable gas is selected from the group consisting of neon-argon, xenon-oxygen, and krypton-neon.

23. The colored light-emitting panel of claim 19, further comprising colored filters applied over each of the plurality of sockets for converting the emitted radiation from each of the plurality of micro-components into red, green, or blue visible light.

24. The colored light-emitting panel of claim 19, wherein the emitted radiation is ultraviolet radiation, and further wherein each of the plurality of micro-components is at least partially coated with phosphor in order to convert the ultraviolet radiation into red, green, or blue visible light.

25. The colored light-emitting panel of claim 19, wherein the emitted radiation is ultraviolet radiation, and further wherein each of the plurality of sockets is at least partially coated with phosphor in order to convert the ultraviolet radiation into red, green, or blue visible light.

26. The colored light-emitting panel of claim 19, further comprising means for selecting a particular field of view for the visible light emitted from the light-emitting panel.

27. The colored light-emitting panel of claim 26, wherein the means for selecting a particular field of view is a single lens.

28. The colored light-emitting panel of claim 26, wherein the means for selecting a particular field of view is a plurality of lenses, wherein the ratio of lenses to sockets is 1:1.

29. The colored light-emitting panel of claim 19, wherein the means for applying a voltage comprises at least two electrodes.

* * * * *

UNITED STATES PATENT AND TRADEMARK OFFICE
CERTIFICATE OF CORRECTION

PATENT NO.      : 6,791,264 B2
APPLICATION NO. : 10/303926
DATED           : September 14, 2004
INVENTOR(S)     : Albert Myron Green et al.

It is certified that error appears in the above-identified patent and that said Letters Patent is hereby corrected as shown below:

On the Title Page:
UNDER REFERENCES CITED (56) - U.S. Patent Documents -

Please add:

| | | | |
|---|---|---|---|
| 2002/0024295 Al | 2/28/02  | Miyashita, et al. | 313/495 |
| 2002/0022565 Al | 2/21/02  | Sreeram, et al.   | 501/16  |
| 2002/0017864 Al | 2/14/02  | Watanabe, et al.  | 313/586 |
| 2002/0016075 Al | 2/7/02   | Peng, et al.      | 438/700 |
| 2002/0009536 Al | 1/24/02  | Iguchi, et al.    | 427/10  |
| 2002/0008470 Al | 1/24/02  | Uegaki, et al.    | 313/567 |
| 2001/0053570 Al | 12/20/01 | Kido              | 438/149 |
| 6,322,010       | 11/27/01 | Sasaki, et al.    | 239/568 |
| 6,319,325       | 11/20/01 | Hiratsuka, et al. | 118/718 |
| 6,312,971       | 11/6/01  | Amundson, et al.  | 438/99  |
| 6,312,304       | 11/6/01  | Duthaler, et al.  | 445/24  |
| 2001/0033256 Al | 10/25/01 | Moore             | 345/60  |
| 6,307,319       | 10/23/01 | Lee               | 313/590 |
| 6,304,238       | 10/16/01 | Tsuchida          | 345/87  |
| 6,304,032       | 10/16/01 | Asano             | 313/582 |
| 6,304,031       | 10/16/01 | Wani, et al.      | 313/582 |
| 6,300,932       | 10/9/01  | Albert            | 345/107 |
| 6,300,152       | 10/9/01  | Kim               | 438/30  |
| 6,297,590       | 10/2/01  | Nanto, et al.     | 313/586 |
| 6,296,539       | 10/2/01  | Awaji, et al.     | 445/24  |
| 6,295,040       | 9/25/01  | Nhan, et al.      | 345/60  |
| 6,292,160       | 9/18/01  | Mikoshiba, et al. | 345/60  |
| 6,292,159       | 9/18/01  | Someya, et al.    | 345/60  |
| 6,291,925       | 9/18/01  | Jacobson          | 310/319 |
| 6,288,693       | 9/11/01  | Song, et al.      | 345/68  |
| 6,288,488       | 9/11/01  | Amemiya           | 313/582 |
| 6,285,434       | 9/4/01   | Ma, et al.        | 349/189 |
| 6,285,129       | 9/4/01   | Park, et al.      | 313/586 |
| 6,281,863       | 8/28/01  | Sasaki, et al.    | 345/60  |
| 6,265,826       | 7/24/01  | Miyazaki          | 313/586 |
| 2001/0008825 Al | 7/19/01  | Toyoda, et al.    | 445/24  |
| 6,262,706       | 7/17/01  | Albert, et al.    | 345/107 |
| 6,255,777       | 7/3/01   | Kim, et al.       | 313/582 |
| 6,201,518       | 3/13/01  | Kane, et al.      | 345/60  |
| 6,137,553       | 10/24/00 | Izumi, et al.     | 349/49  |

UNITED STATES PATENT AND TRADEMARK OFFICE
CERTIFICATE OF CORRECTION

PATENT NO. : 6,791,264 B2
APPLICATION NO. : 10/303926
DATED : September 14, 2004
INVENTOR(S) : Albert Myron Green et al.

It is certified that error appears in the above-identified patent and that said Letters Patent is hereby corrected as shown below:

UNDER REFERENCES CITED (56) - U.S. Patent Documents (cont'd):

| | | | |
|---|---|---|---|
| 6,130,655 | 10/10/00 | Lammers | 345/72 |
| 6,097,147 | 8/1/2000 | Baldo et al. | 313/506 |
| 6,091,874 | 7/18/00 | Higashi, et al. | 384/130 |
| 6,091,380 | 7/18/00 | Hashimoto et al. | 345/60 |
| 6,091,195 | 7/18/00 | Forrest et al. | 313/504 |
| 8,087,196 | 7/11/00 | Sturm et al. | 438/29 |
| 6,080,606 | 6/27/00 | Gleskova et al. | 438/151 |
| 6,079,814 | 6/27/00 | Lean, et al. | 347/55 |
| 6,072,276 | 6/6/00 | Okajima | 313/581 |
| 6,069,443 | 5/30/00 | Jones et al. | 313/504 |
| 6,049,366 | 4/11/00 | Hakemi et al. | 349/86 |
| 6,048,630 | 4/11/00 | Burrows et al. | 428/690 |
| 6,048,469 | 4/11/00 | Xiang, et al. | 252/301.6 R |
| 6,046,543 | 4/4/00 | Bulovic et al. | 313/504 |
| 6,045,930 | 4/4/00 | Thompson et al. | 428/690 |
| 6,039,619 | 3/21/00 | Kang et al. | 445/24 |
| 6,038,002 | 3/14/00 | Song | 349/43 |
| 6,037,918 | 3/14/00 | Hansen et al. | 345/74 |
| 6,037,710 | 3/14/00 | Poole et al. | 313/422 |
| 6,033,547 | 3/7/00 | Trau et al. | 204/622 |
| 6,030,715 | 2/29/00 | Thompson et al. | 428/690 |
| 6,030,269 | 2/29/00 | Drumm | 445/52 |
| 6,025,097 | 2/15/00 | Drumm | 430/7 |
| 6,023,259 | 2/8/00 | Howard et al. | 345/76 |
| 6,022,652 | 2/8/00 | Haven et al. | 430/26 |
| 6,019,657 | 2/1/00 | Chakvorty et al. | 445/24 |
| 6,017,584 | 1/25/00 | Albert et al. | 427/213.3 |
| 6,013,538 | 1/11/00 | Burrows et al. | 438/22 |
| 6,002,198 | 12/14/99 | Spindt et al. | 313/292 |
| 5,990,620 | 11/23/99 | Lepselter | 313/585 |
| 5,990,614 | 11/23/99 | Spindt | 313/495 |
| 5,986,409 | 11/16/99 | Farnworth et al. | 315/169.4 |
| 5,985,460 | 11/16/99 | Wang et al. | 428/426 |
| 5,984,747 | 11/16/99 | Bhagavatula et al. | 445/24 |
| 5,975,683 | 11/2/99 | Smith, et al. | 347/55 |
| 5,969,472 | 10/19/99 | Kisner | 313/484 |
| 5,967,871 | 10/19/99 | Kaake, et al. | 445/24 |
| 5,965,109 | 10/12/99 | Lohrmann | 424/9.52 |

UNITED STATES PATENT AND TRADEMARK OFFICE
CERTIFICATE OF CORRECTION

PATENT NO.        : 6,791,264 B2
APPLICATION NO. : 10/303926
DATED              : September 14, 2004
INVENTOR(S)      : Albert Myron Green et al.

It is certified that error appears in the above-identified patent and that said Letters Patent is hereby corrected as shown below:

UNDER REFERENCES CITED (56) - U.S. Patent Documents (cont'd):

| | | | |
|---|---|---|---|
| 5,964,630 | 10/12/99 | Slusarczuk et al. | 445/25 |
| 5,953,587 | 9/14/99 | Forrest et al. | 438/99 |
| 5,949,513 | 9/7/99 | Ma, et al. | 349/187 |
| 5,945,174 | 8/31/99 | Shaw et al. | 427/509 |
| 5,920,080 | 7/6/99 | Jones | 257/40 |
| 5,917,646 | 6/29/99 | Sheridon | 359/296 |
| 5,914,150 | 6/22/66 | Porter et al. | 427/77 |
| 5,913,704 | 6/22/99 | Spindt et al. | 445/24 |
| 5,898,266 | 4/27/99 | Spindt et al. | 313/495 |
| 5,897,414 | 4/27/99 | Bergeron et al. | 445/3 |
| 5,865,657 | 2/2/99 | Haven et al. | 445/24 |
| 5,862,054 | 1/19/99 | Li | 364/468.28 |
| 5,853,446 | 12/29/98 | Carre, et al. | 65/17.3 |
| 5,844,363 | 12/1/98 | Gu et al. | 313/506 |
| 5,837,221 | 11/17/98 | Bernstein, et al. | 424/9.52 |
| 5,825,451 | 10/20/98 | Ma, et al. | 349/187 |
| 5,815,306 | 9/29/98 | Sheridon et al. | 359/296 |
| 5,811,833 | 9/22/98 | Thompson | 257/40 |
| 5,798,604 | 8/25/98 | Duboc, Jr., et al. | 313/495 |
| 5,793,158 | 8/11/98 | Wedding, Sr. | 313/493 |
| 5,788,814 | 8/4/98 | Sun, et al. | 204/297R |
| 5,777,782 | 7/7/98 | Sheridon | 359/296 |
| 5,757,139 | 5/26/98 | Forrest et al. | 315/169.3 |
| 5,757,131 | 5/26/98 | Tsuchiya | 375/582 |
| 5,757,026 | 5/26/98 | Forrest et al. | 257/40 |
| 5,755,944 | 5/26/98 | Haven et al. | 204/486 |
| 5,747,931 | 5/5/98 | Riddle et al. | 313/581 |
| 5,746,635 | 5/5/98 | Spindt et al. | 445/24 |
| 5,725,787 | 3/10/98 | Curtin et al. | 216/25 |
| 5,721,160 | 2/24/98 | Forrest et al. | 438/28 |
| 5,707,745 | 1/13/98 | Forrest et al. | 428/432 |
| 5,703,436 | 12/30/97 | Forrest et al. | 313/506 |
| 5,686,790 | 11/11/790 | Curtin et al. | 313/493 |
| 5,675,212 | 10/7/97 | Schmid et al. | 313/422 |
| 5,674,351 | 10/7/97 | Lovoi | 156/629.1 |
| 5,514,934 | 5/7/96 | Matsumoto et al. | 313/607 |
| 5,510,678 | 4/23/96 | Sakai, et al. | 315/58 |
| 5,501,871 | 3/26/96 | Henderson | 427/160 |

UNITED STATES PATENT AND TRADEMARK OFFICE
CERTIFICATE OF CORRECTION

| | |
|---|---|
| PATENT NO. | : 6,791,264 B2 |
| APPLICATION NO. | : 10/303926 |
| DATED | : September 14, 2004 |
| INVENTOR(S) | : Albert Myron Green et al. |

It is certified that error appears in the above-identified patent and that said Letters Patent is hereby corrected as shown below:

UNDER REFERENCES CITED (56) - U.S. Patent Documents (cont'd):

| | | | |
|---|---|---|---|
| 5,500,287 | 3/19/96 | Henderson | 428/403 |
| 5,396,149 | 3/7/95 | Kwon | 313/486 |
| 5,315,129 | 5/24/94 | Forrest et al. | 257/21 |
| 5,150,007 | 9/22/92 | Andreadakis | 313/586 |
| 5,126,632 | 6/30/92 | Parker | 313/634 |
| 5,075,597 | 12/24/91 | Deschamps, et al. | 315/169.4 |
| 5,068,916 | 11/26/91 | Harrison et al. | 455/39 |
| 5,062,916 | 11/5/91 | Aufderheide et al. | 156/269 |
| 5,030,888 | 7/9/91 | Salavin, et al. | 315/169.4 |
| 5,019,807 | 5/28/91 | Stapleton, et al. | 340/718 |
| 4,912,364 | 3/27/90 | Holló et al. | 313/623 |
| 4,887,003 | 12/12/89 | Parker | 313/634 |
| 4,843,281 | 6/27/89 | Mendelsohn | 313/587 |
| 4,833,463 | 5/23/89 | Dick, et al. | 340/775 |
| 4,728,864 | 3/1/98 | Dick | 315/169.3 |
| 4,697,123 | 9/29/87 | Shinoda, et al. | 315/169.4 |
| 4,658,269 | 4/14/87 | Rezanka | 346/75 |
| 4,654,561 | 3/31/87 | Shelton | 315/111.71 |
| 4,591,847 | 5/27/86 | Criscimagna, et al. | 340/776 |
| 4,563,617 | 1/7/86 | Davidson | 315/312 |
| 4,554,537 | 11/19/85 | Dick | 340/775 |
| 4,534,743 | 8/13/85 | D'Onofrio, et al. | 445/24 |
| 4,429,303 | 1/31/84 | Aboelfotoh | 340/701 |
| 4,393,326 | 7/12/83 | Kamegaya, et al. | 313/582 |
| 4,386,358 | 5/31/83 | Fischbeck | 346/1.1 |
| 4,379,301 | 4/5/83 | Fischbeck | 346/1.1 |
| 4,303,433 | 12/1/81 | Torobin | 65/21.4 |
| 4,035,690 | 7/12/77 | Roeber | 315/169 TV |
| 4,027,246 | 5/31/77 | Caccoma, et al. | 235/151.1 |
| 3,998,618 | 12/21/76 | Kreick et al. | 65/105 |
| 3,990,068 | 11/2/76 | Mayer, et al. | 340/324M |
| 3,969,651 | 7/13/76 | Greeson, Jr. | 315/169 TV |
| 3,848,248 | 11/12/74 | MacIntyre, Jr. | 340/324 M |
| 3,755,027 | 8/28/73 | Gilsing | 156/67 |
| 3,704,052 | 11/28/72 | Coleman | 316/17 |
| 3,646,384 | 2/29/72 | Lay | 313/109.5 |
| 3,559,190 | 1/26/71 | Blitzer et al. | 340/173 |

UNITED STATES PATENT AND TRADEMARK OFFICE
CERTIFICATE OF CORRECTION

| | |
|---|---|
| PATENT NO. | : 6,791,264 B2 |
| APPLICATION NO. | : 10/303926 |
| DATED | : September 14, 2004 |
| INVENTOR(S) | : Albert Myron Green et al. |

It is certified that error appears in the above-identified patent and that said Letters Patent is hereby corrected as shown below:

On the Title Page:
UNDER REFERENCES CITED (56) - Foreign Patent Documents -

Please add:

| | | | |
|---|---|---|---|
| JP 10-3869 | 1/6/98 | Canon, Inc. | H01J/31/12 |
| JP 4-287397 | 10/12/92 | NEC Corp. | H05K/9/00 |

On the Title Page:
UNDER REFERENCES CITED (56) - Other Publications -

Please add:

Written Opinion for Application No. PCT/US01/42782, dated December 31, 2002 (mailing date)

International Search Report for Application No. PCT/US01/42807, dated December 8, 2002 (mailing date)

International Search Report for Application No. PCT/US01/51439, dated September 23, 2002 (mailing date)

Written Opinion for Application No. PCT/US01/42807, dated September 17, 2002 (mailing date)

International Search Report for Application No. PCT/US01/42807, dated May 20, 2002 (mailing date)

International Search Report for Application No. PCT/US01/42782, dated April 11, 2002 (mailing date)

Sheats, James, "Introduction to Organic Light-Emitting Diodes (OLEDs)" [online], [retrieved on May 9, 2002], 8 pp., Retrieved from the Internet: http://www.rolltronics.com/intro_oled.htm Sauvante, Michael, "Roll-to-Roll Manufacturing" [online], [retrieved on May 9, 2002], 4 pp., Retrieved from the Internet: http://www.rolltronics.com/roll2roll.htm

UNITED STATES PATENT AND TRADEMARK OFFICE
CERTIFICATE OF CORRECTION

PATENT NO.         : 6,791,264 B2
APPLICATION NO. : 10/303926
DATED                  : September 14, 2004
INVENTOR(S)        : Albert Myron Green et al.

It is certified that error appears in the above-identified patent and that said Letters Patent is hereby corrected as shown below:

UNDER REFERENCES CITED (56) - Other Publications - (cont'd):

Veronis, Georgios and Inan, Umran S., "Optimization of the Luminous Efficiency of Plasma Display Panels Using Numerical Modeling" [online], [retrieved on March 13, 2002], 8 pp., Retrieved from the Internet: http://www-star.stanford.edu/~vlf/plasma_display/index.htm Smilgys, Russell, et al., "Progress Toward Roll Processing of Solar Reflective Material," Proceedings of Solar Forum 2001 Solar Energy: The Power to Choose, Washington, DC, 8 pp., April 21-25, 2001

Srinivasan, Uthara, et al., "Microstructure to Substrate Self-Assembly Using Capillary Forces," Journal of Microelectromechanical Systems, Vol. 10, No. 1, March, 2001, pp. 17-17-24

Chutinan, Alongkarn and Noda, Susumu, "Waveguides and Waveguide Bends in Two-Dimensional Photonic Crystal Slabs," The American Physical Society, Vol. 62, No. 7, 5 pp., August 15, 2000

"Rolltronics" [online], February 20, 2000 [retrieved on March 12, 2000], 13 pp., Retrieved from the Internet: http://www.rolltronics.com "Electronics & Telecommunications" [online], LG Electronics, Copyright 2001 [retrieved on 11/7/2001], 1 p., Retrieved from the Internet: http://www.lg.co.kr/English/company/electronic/index.jsp?code=A3

"New Product" [online], LG Electronics, Copyright 2001 [retrieved on 11/7/2001], 1 p., Retrieved from the Internet: http://www.lge.com "Monitor" [online], LG Electronics, Copyright 2001 [retrieved on 11/7/2001], 2 pp., Retrieved from the Internet: http://www.lgeus.com/Product/Monitor/newmonitors.asp "LG Electronics Introduces 42-Inch Digital PDP TV" [online], LG Electronics, Copyright 2001 [retrieved on 11/7/2001], 2 pp., Retrieved from the Internet: http://www.pdpdisplay.com/eng/news/e_read.as?nSeqno=22

"LG PDP Now Available at World Renowned Harrods Department Store" [online], LG Electronics, Copyright 2001 [retrieved on 11/7/2001], 2 pp., Retrieved from the Internet: http://www.pdpdisplay.com/eng/news/e_read.asp?nSeqno21

UNITED STATES PATENT AND TRADEMARK OFFICE
CERTIFICATE OF CORRECTION

PATENT NO.       : 6,791,264 B2
APPLICATION NO. : 10/303926
DATED            : September 14, 2004
INVENTOR(S)      : Albert Myron Green et al.

It is certified that error appears in the above-identified patent and that said Letters Patent is hereby corrected as shown below:

UNDER REFERENCES CITED (56) - Other Publications - (cont'd):

"LG Electronics Becomes First in Korea to Export PDP Module" [online], LG Electronics, Copyright 2001 [retrieved on 11/7/2001], 2 pp., Retrieved from the Internet: http://www.pdpdisplay.com/eng/news/e_read.asp?nSeqNo=19&type=&word=

"LG Electronics – To the Top in PDP Business" [online], LG Electronics, Copyright 2001 [retrieved on 11/7/2001], 2 pp., Retrieved from the Internet: http://www.pdpdisplay.com/eng/news/e_read.asp?nSeqNo=16&type=&word=

"LG Electronics Becomes the First in Korea to Export PDP" [online], LG Electronics, Copyright 2001 [retrieved on 11/7/2001], 2 pp., Retrieved from the Internet: http://www.pdpdisplay.com/eng/news/e_read.asp?nSeqNo=14&type=&word=

"LG Electronics Held the Ceremony for the Completion of the PDP Factory" [online], LG Electronics, Copyright 2001 [retrieved on 11/7/2001], 2 pp., Retrieved from the Internet: http://www.pdpdisplay.com/eng/news/e_read.asp?nSeqNo=l3&type=&word "Runco PlasmaWall Systems with Vivex Processing" [online], Copyright 2001 [retrieved on 1/17/2002], 2 pp., Retrieved from the Internet: http://www.runco.com/Products/Plasma/Default.htm "Runco PlasmaWall PL-42cx" [online], Copyright 2001 [retrieved on 1/17/2002], 2 pp., Retrieved from the Internet: http://www.runco.com/Products/Plasma/PL42cx.htm "Runco PlasmaWall P1-50c" [online], Copyright 2001 [retrieved on 1/17/2002], 2 pp., Retrieved from the Internet: http://www.runco.com/Products/Plasma/PL50c.htm "Runco PlasmaWall™ PL-61cx" [online], Copyright 2001 [retrieved on 1/17/2002], 2 pp., Retrieved from the Internet: http://www.runco.com/Products/Plasma/PL61.htm Alien Technology Corporation's Technology Overview; copyright Ó 2000, Alien TechnologyÔ; http://www.alientechnology.com/d/technology/overview.html Anonymous, Alien Technology Corporation White Paper – Fluidic Self Assembly, Alien Technology Corp., October 1999, pp. 1-7.

UNITED STATES PATENT AND TRADEMARK OFFICE
CERTIFICATE OF CORRECTION

PATENT NO. : 6,791,264 B2
APPLICATION NO. : 10/303926
DATED : September 14, 2004
INVENTOR(S) : Albert Myron Green et al.

It is certified that error appears in the above-identified patent and that said Letters Patent is hereby corrected as shown below:

UNDER REFERENCES CITED (56) - Other Publications - (cont'd):

Shin, Y. K., Lee, J. K., Shon, C. H., "Two-Dimensional Breakdown Characteristics of PDP Cells for Varying Geometry," IEEE Transactions on Plasma Science, Vol. 27, No. 1, February, 1999, pp. 14-15

Raulf, S., Kushner, M. J., "Operation of a Coplanar-Electrode Plasma Display Panel Cell," IEEE Transactions on Plasma Science, Vol. 27, No. 1, February 1999, pp. 10-11

Kurihara, M., Makabe, T., "Two-Dimensional Modeling of a Micro-Cell Plasma in Xe Driven by High Frequency," IEEE Transactions on Plasma Science, Vol. 27, No. 5, October, 1999, pp. 1372-1378

Peterson, "Rethinking Ink" [online], Science News, Vol. 153, No. 25, June 20, 1998 [retrieved on December 4, 2002], 7 pp., Retrieved from the Internet: http://www.sciencenews.org/sn_arc98/6_20_98/bob2.htm "Transparent Conductive Coatings," Copyright 1998, 4 pp.

Lin, Yi-Zhen, et al., "A New Method of Analyzing the Light Transmission in Leaky and Absorbing Planar Waveguides," IEEE Photonics Technology Letters, Vol. 9, No. 9, September, 1997, pp. 1241-

Jacobson, et al., "The Last Book" [online], IBM Systems Journal, Vol. 36, No. 3, 1997 [retrieved on December 4, 2002], 6 pp., Retrieved from the Internet: http://www.research.ibm.com/journal/sj/363/Jacobson.html Stearns, Thomas H., "Flexible Printed Circuitry," 6 pp., 1996

"Flat Panel Displays In Perspective," 44 pp., September, 1995

UNITED STATES PATENT AND TRADEMARK OFFICE
CERTIFICATE OF CORRECTION

PATENT NO. : 6,791,264 B2
APPLICATION NO. : 10/303926
DATED : September 14, 2004
INVENTOR(S) : Albert Myron Green et al.

It is certified that error appears in the above-identified patent and that said Letters Patent is hereby corrected as shown below:

UNDER REFERENCES CITED (56) - Other Publications - (cont'd):

Franjione, et al., "The Art and Science of Microencapsulation" [online] Technology Today, Summer, 1995 [retrieved on December 4, 2002], 10 pp., Retrieved from the Internet: http://www.swri.edu/3pubs/ttoday/summer95/microeng.htm Signed and Sealed this Thirtieth Day of October, 2007

JON W. DUDAS
*Director of the United States Patent and Trademark Office*